(12) United States Patent
Wu et al.

(10) Patent No.: US 9,226,927 B2
(45) Date of Patent: Jan. 5, 2016

(54) GAMMA SECRETASE INHIBITORS

(75) Inventors: Wen-Lian Wu, Edison, NJ (US); Duane A. Burnett, Wayland, MA (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 14/342,953

(22) PCT Filed: Sep. 4, 2012

(86) PCT No.: PCT/US2012/053598
§ 371 (c)(1),
(2), (4) Date: Mar. 5, 2014

(87) PCT Pub. No.: WO2013/036464
PCT Pub. Date: Mar. 14, 2013

(65) Prior Publication Data
US 2014/0227302 A1 Aug. 14, 2014

Related U.S. Application Data

(60) Provisional application No. 61/532,842, filed on Sep. 9, 2011.

(51) Int. Cl.
| | |
|---|---|
| *C07D 493/04* | (2006.01) |
| *A61K 31/4155* | (2006.01) |
| *A61K 31/4245* | (2006.01) |
| *A61K 31/4433* | (2006.01) |
| *A61K 31/497* | (2006.01) |
| *A61K 31/501* | (2006.01) |
| *A61K 45/06* | (2006.01) |

(52) U.S. Cl.
CPC ........... *A61K 31/501* (2013.01); *A61K 31/4155* (2013.01); *A61K 31/4245* (2013.01); *A61K 31/4433* (2013.01); *A61K 31/497* (2013.01); *A61K 45/06* (2013.01); *C07D 493/04* (2013.01)

(58) Field of Classification Search
CPC ............. C07D 493/04; A61K 31/4155; A61K 31/4245; A61K 31/4433; A61K 31/497; A61K 31/501
See application file for complete search history.

(56) References Cited

U.S. PATENT DOCUMENTS

| | | |
|---|---|---|
| 2007/0197581 A1 | 8/2007 | Asberom et al. |
| 2010/0222338 A1 | 9/2010 | Zhong et al. |
| 2011/0054013 A1 | 3/2011 | Clader |

FOREIGN PATENT DOCUMENTS

| | | | |
|---|---|---|---|
| WO | WO 2009/008980 | * | 1/2009 |
| WO | WO2009011851 | | 1/2009 |

OTHER PUBLICATIONS

Mangialasche et al., LancetNeurol. 2010; 9: p. 702-716.*
N. Engl. J. Med., vol. 369, Jul. 25, 2013, p. 341-350.*
Neurology Today, vol. 10, Feb. 4, 2010, Issue 3; p. 16-17.*

* cited by examiner

*Primary Examiner* — Valerie Rodriguez-Garcia
(74) *Attorney, Agent, or Firm* — J. Eric Thies; John C. Todaro

(57) ABSTRACT

Disclosed herein are compounds of Formula (I) (I) and pharmaceutically acceptable salts thereof, wherein each of the substituents is given the definition as set forth in the specification and claims. Also disclosed are pharmaceutical compositions containing the compound of Formula (I) and use of the compound in the treatment of neurodegenerative diseases or conditions such as Alzheimer's disease.

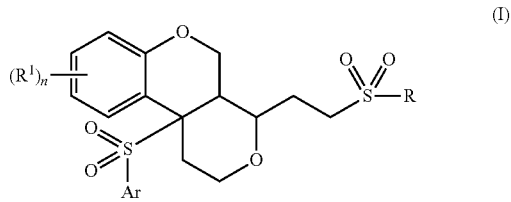

(I)

12 Claims, No Drawings

GAMMA SECRETASE INHIBITORS

CROSS REFERENCE TO RELATED APPLICATIONS

This application is a U.S. National Phase application under 35 U.S.C. §371 of PCT Application No. PCT/US2012/053598, filed Sep. 4, 2012, which claims priority under 35 U.S.C. §119(e) from U.S. Ser. No. 61/532,842 filed Sep. 9, 2011.

BACKGROUND OF THE INVENTION

Alzheimer's disease is a disease characterized by degeneration and loss of neurons and also by the formation of senile plaques and neurofibrillary change. Presently, treatment of Alzheimer's disease is limited to symptomatic therapies with a symptom-improving agent represented by an acetylcholinesterase inhibitor, and the basic remedy which prevents progress of the disease has not been developed. A method of controlling the cause of onset of pathologic conditions needs to be developed for creation of the basic remedy of Alzheimer's disease.

Aβ protein, which is a metabolite of amyloid precursor protein (hereinafter referred to as APP), is considered to be greatly involved in degeneration and loss of neurons as well as onset of demential conditions (for example, see Klein W L, et al Proceeding National Academy of Science USA, Sep. 2, 2003, 100(18), p. 10417-22), suggesting a molecular basis for reversible memory loss.

Nitsch R M, and 16 others, *Antibodies against β-amyloid slow cognitive decline in Alzheimer's disease*, Neuron, May 22, 2003, 38(4), p. 547-554) suggest that the main components of Aβ protein are Aβ40 consisting of 40 amino acids and Aβ42 having two additional amino acids at the C-terminal. The Aβ40 and Aβ42 tend to aggregate (for example, see Jarrell J T et al, *The carboxy terminus of the β amyloid protein is critical for the seeding of amyloid formation: implications for the pathogenesis of Alzheimer's disease*, Biochemistry, May 11, 1993, 32(18), p. 4693-4697) and constitute the main components of senile plaques (for example, (Glenner G G, et al, *Alzheimer's disease: initial report of the purification and characterization of a novel cerebrovascular amyloid protein*, Biochemical and Biophysical Research Communications, May 16, 1984, 120(3), p. 885-90. See also Masters C L, et al, *Amyloid plaque core protein in Alzheimer's disease and Down's syndrome*, Proceeding National Academy of Science USA, June 1985, 82(12), p. 4245-4249.).

Furthermore, it is known that mutations of APP and presenelin genes, which are observed in familial Alzheimer's disease, increase production of Aβ40 and Aβ42 (for example, see Gouras G K, et al, *Intraneuronal Aβ142 accumulation in human brain*, American Journal of Pathology, January 2000, 156(1), p. 15-20. Also, see Scheuner D, et al, Nature Medicine, August 1996, 2(8), p. 864-870; and Forman M S, et al, *Differential effects of the Swedish mutant amyloid precursor protein on β-amyloid accumulation and secretion in neurons and nonneuronal cells*, Journal of Biological Chemistry, Dec. 19, 1997, 272(51), p. 32247-32253.). Therefore, compounds which reduce production of Aβ40 and Aβ42 are expected to be agents for controlling progress of Alzheimer's disease or for preventing the disease.

These Aβs are produced when APP is cleaved by beta secretase and subsequently cleaved by gamma secretase. In consideration of this, creation of inhibitors of γ-secretase and β-secretase has been attempted for the purpose of reducing production of Aβs. Many of these known secretase inhibitors are peptides or peptidomimetics such as L-685,458. L-685,458, an aspartyl protease transition state mimic, is a potent inhibitor of γ-secretase activity (Biochemistry, Aug. 1, 2000, 39(30), p. 8698-8704).

There is a need for new compounds, formulations, treatments and therapies to treat diseases and disorders associated with Aβ. It is, therefore, an object of this invention to provide compounds useful in the treatment or prevention or amelioration of such diseases and disorders.

SUMMARY OF THE INVENTION

Compounds of this invention herein termed gamma secretase inhibitors have the structure of Formula (I)

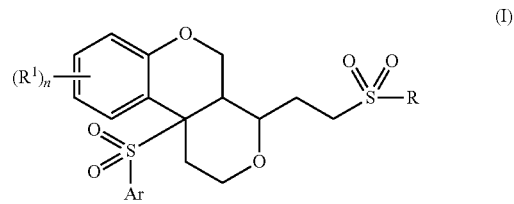

(I)

or a pharmaceutically acceptable salt thereof, wherein
R is a 5-6 membered heteroaryl containing 1-2 nitrogen atoms optionally substituted with one $L^1$ group; or a —(C1-C6)alkyl(5-6 membered)heteroaryl containing 1-3 heteroatoms selected from N and O optionally substituted with one $L^1$ group, with the proviso that the (5-6 membered)heteroaryl of the —(C1-C6)alkyl(5-6 membered)heteroaryl is not furanyl;
$R^1$ is independently selected from the group consisting of halogen, —(C1-C6)alkyl, —CN, —CF$_3$, —O—(C1-C6)alkyl, —O-(halo(C1-C6)alkyl), —C(O)—O—(C1-C6)—OH-substituted (C1-C4)alkyl, halo(C1-C6)alkyl, —(C1-C4)alkoxy-OH, —(C1-C4)alkoxy(C1-C4)alkoxy and —S(O)$_2$(C1-C6)alkyl; n is 0, 1, 2, or 3;
Ar is selected from the group consisting of phenyl optionally substituted with 1 or 2 $L^2$ groups, and pyridyl optionally substituted with 1 or 2 $L^2$ groups;
$L^1$ is independently selected from the group consisting of —OCH$_3$, —NH$_2$, =O, and (C1-C5)alkyl; and
$L^2$ is independently selected from the group consisting of halogen, (C1-C6)alkyl, —CN, —CF$_3$, —O—(C1-C6)alkyl, —O-(halo(C1-C6)alkyl), —C(O)—O—(C1-C6)alkyl, —OH- substituted (C1-C6)alkyl, halo(C1-C6)alkyl, —OH-substituted (C1-C4)alkoxy, —(C1-C4)alkoxy(C1-C4)alkoxy and —S(O)$_2$(C1-C6)alkyl.

In an embodiment, the present invention provides for pharmaceutical compositions comprising at least one compound of Formula (I). In another embodiment, the present invention provides for methods for inhibiting gamma secretase activity comprising administering a therapeutically effective amount of at least one compound of Formula (I) to a patient afflicted with a disease or condition amenable to treatment by inhibition of gamma secretase, e.g., Alzheimer's disease.

DETAILED DESCRIPTION OF THE INVENTION

As used above, and throughout this disclosure, the following terms, unless otherwise indicated, shall be understood to have the following meanings:

"At least one" means there is at least one, and examples include 1, 2 or 3, or 1 or 2, or 1.

"One or more" means the same as "at least one."

"Patient" and "subject" means an animal, such as a mammal, e.g., a human being, and is preferably a human being.

"Alkyl" means an aliphatic hydrocarbon group, which may be straight or branched and comprising about 1 to about 6 carbon atoms in the chain or about 1 to about 2 or 3 carbon atoms in the chain. Branched means that one or more lower alkyl groups such as methyl, ethyl or propyl, are attached to a linear alkyl chain. Non-limiting examples of suitable alkyl groups include methyl, ethyl, n-propyl, isopropyl and t-butyl.

"Halogen" means fluorine, chlorine, bromine, or iodine. Fluorine, chlorine and bromine are preferred. A substituent which is a halogen atom means —F, —Cl, —Br, or —I, and "halo" means fluoro, chloro, bromo or iodo substituents bonded to the moiety defined, e.g., "haloalkyl" means an alkyl, as defined above, wherein one or more of the bonding positions on the alkyl moiety typically occupied by hydrogen atoms are instead occupied by a halo group, e.g., trifluoromethyl.

"Heteroaryl" means an aromatic monocyclic ring system comprising about 5 to about 6 ring atoms in which one or more of the atoms in the ring system is an element other than carbon, for example nitrogen or oxygen or in combination. Any —NH in a heteroaryl ring may exist in protected form, for example, as an —N(Boc), —N(CBz), —N(Tos) group and the like; such protected forms are also considered part of this invention. Non-limiting examples of suitable monocyclic heteroaryl rings include pyrrole, oxazole, imidazole, pyrazole, isooxazole, 1,2,3, oxadiazole, 1,2,4, oxadiazole, 1,2,3-triazole, 2H-pyran, 4H-pyran, pyridine, pyrimidine, pyridazine, pyrazine, 1,3,5, triazine, pyrrole.

"Hydroxy (—OH) substituted alkyl" means an alkyl group substituted with a hydroxy (—OH) group in which alkyl is as previously defined. Preferred hydroxyalkyls contain lower alkyl. Non-limiting examples of suitable hydroxyalkyl groups include hydroxymethyl and 2-hydroxyethyl.

"Alkoxy" means an —O—(C1-C4)alkyl group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkoxyalkoxy" means (C1-C4)alkoxy-(C1-C4)alkoxy" and refers to alkoxy groups as defined above wherein at least one of the hydrogen atoms of the lower alkoxy group is replaced by an alkoxy group as defined above. Among the preferred lower alkoxyalkoxy groups are 2-methoxy-ethoxy and 3-methoxy-propoxy.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties. For example, a phenyl optionally substituted with an indicated group of substituents includes unsubstituted phenyl as well as phenyl substituted with any of the indicated substituents.

It should also be noted that any carbon atom as well as any heteroatom with unsatisfied valences in the text, schemes, examples, Tables, etc. herein is assumed to have the sufficient number of hydrogen atom(s) to satisfy the valences.

When a functional group in a compound is termed "protected", this means that the group is present in modified form to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in Organic Synthesis (1991), Wiley, N.Y., herein incorporated by reference in its entirety.

"Effective amount" or "therapeutically effective amount" is meant to describe an amount of compound or a composition of the present invention effective in inhibiting the production and/or deposition of amyloid protein, and thus producing the desired therapeutic, ameliorative, inhibitory or preventative effect.

This invention provides compounds that are inhibitors (e.g., antagonists) of gamma-secretase (also termed "γ-secretase") and have the Formula (I):

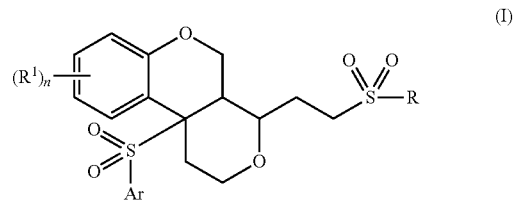

or a pharmaceutically acceptable salt thereof, wherein

R is a 5-6 membered heteroaryl containing 1-2 nitrogen atoms optionally substituted with one $L^1$ group; or a —(C1-C6)alkyl(5-6 membered)heteroaryl containing 1-3 heteroatoms selected from N and O optionally substituted with one $L^1$ group, with the proviso that the (5-6 membered)heteroaryl of the —(C1-C2)alkyl(5-6 membered)heteroaryl is not furanyl;

$R^1$ is independently selected from the group consisting halogen, (C1-C6)alkyl, —CN, —CF$_3$, —O—(C1-C6)alkyl, —O-(halo(C1-C6)alkyl), —C(O)—O—(C1-C6)—OH-substituted (C1-C4)alkyl, halo(C1-C6)alkyl, —(C1-C4)alkoxy-OH, —(C1-C4)alkoxy(C1-C4)alkoxy and —S(O)$_2$(C1-C6)alkyl; n is 0, 1, 2, or 3;

Ar is selected from the group consisting of phenyl optionally substituted with 1 or 2 $L^2$ groups, and pyridyl optionally substituted with 1 or 2 $L^2$ groups;

$L^1$ is independently selected from the group consisting of —OCH$_3$, —NH$_2$, =O, and (C1-C5)alkyl (e.g., methyl, propyl, butyl and pentyl); and $L^2$ is independently selected from the group consisting of halogen, (C1-C6)alkyl, —CN, —CF$_3$, —O—(C1-C6)alkyl, —O-(halo(C1-C6)alkyl), —C(O)—O—(C1-C6)alkyl, —OH- substituted (C1-C6)alkyl, -halo(C1-C6)alkyl, —OH-substituted (C1-C4)alkoxy, —(C1-C4)alkoxy(C1-C4)alkoxy and —S(O)$_2$(C1-C6)alkyl.

The compounds of the invention have been found to be inhibitors of gamma-secretase activity and are believed to be useful in providing treatment of conditions or diseases which can be treated by inhibition of gamma-secretase activity, for example, Alzheimer's disease, Down's Syndrome, mild cognitive impairment, glaucoma, cerebral amyloid angiopathy, stroke, dementia, microgliosis, brain inflammation, traumatic brain injury and olfactory function loss, and certain cancers, for example, T cell acute lymphoblastic leukemia, ovarian cancer, and lung cancers, e.g., non-small-cell lung carcinomas.

In one embodiment of the compounds of Formula (I), n is 2, each R¹ is the same or different halogen, and the R¹ groups are bound to the phenyl moiety as shown in Formula (II):

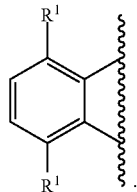

In another embodiment of the compounds of Formula (I), in particular when n is 2, wherein the R¹ groups are bound to the phenyl moiety as shown in Formula (II), the halogen of R¹ is fluoro.

In another embodiment of the compounds of Formula (I), in particular, when n is 2, wherein the R¹ groups are bound to the phenyl moiety as shown in Formula (II), and R¹ is fluoro, Ar is selected from the group consisting of p-Cl-phenyl-, p-CN-phenyl-, p-CF₃-phenyl-, pyridyl, and pyridyl substituted with 1 or 2 substituents independently selected from the group consisting of halogen, —(C1-C6)alkyl, —CN, —CF₃, —O—(C1-C6)alkyl, —O-halo(C1-C6)alkyl, —C(O)—O—(C1-C6)alkyl, —OH-substituted (C1-C6)alkyl, -halo(C1-C6)alkyl, —OH substituted (C1-C4)alkoxy and —(C1-C4)alkoxy(C1-C4)alkoxy.

In another embodiment of the compounds of Formula (I), in particular, when n is 2, wherein the R¹ groups are bound to the phenyl moiety as shown in Formula (II), and R¹ is fluoro, Ar is p-Cl-phenyl.

In another embodiment of the compounds of Formula (I), R is a 5-6 membered heteroaryl containing 1-2 nitrogen atoms optionally substituted with one L¹ group.

In another embodiment of the compounds of Formula (I), the 5-6 membered heteroaryl containing 1-2 nitrogen atoms optionally substituted with one L¹ group is selected from pyridinyl, pyrimidinyl, pyradazinyl and pyrazinyl.

In another embodiment of the compounds of Formula (I), R is a (C1-C6)alkyl(5-6 membered)heteroaryl containing 1-3 heteroatoms selected from N and O optionally substituted with one L¹ group. In particularly useful embodiments of the compounds of Formula (I), R is a (C1-C2)alkyl(5-6 membered)heteroaryl.

In another embodiment of the compounds of Formula (I), the (5-6 membered)heteroaryl of the (C1-C6)alkyl(5-6 membered)heteroaryl containing 1-3 heteroatoms selected from N and O optionally substituted with one L¹ group is selected from pyridinyl, pyrazolinyl and 1, 2, 4 oxadiazolyl.

In another embodiment, the compounds of Formula (I) have the following Formula (IA)

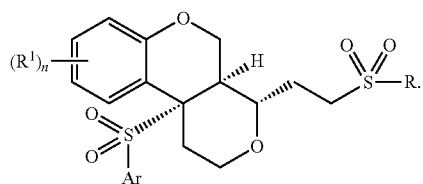

In another embodiment of the compounds of Formula (IA), Ar is p-Cl-phenyl, n is 2, each R¹ is the same or different halogen, and the R¹ groups are bound to the phenyl moiety as shown in Formula (II):

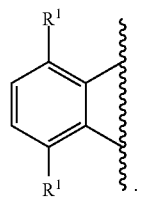

In another embodiment of the compounds of Formula (IA) wherein Ar is p-Cl-phenyl, n is 2, each R¹ is the same or different halogen, and the R¹ groups are bound to the phenyl moiety as shown in Formula (II), R is a (C1-C6)alkyl(5-6 membered)heteroaryl containing 1-3 heteroatoms selected from N and O optionally substituted with one L¹ group.

In another embodiment of the compounds of Formula (IA), wherein Ar is p-Cl-phenyl, n is 2, each R¹ is the same or different halogen, and the R¹ groups are bound to the phenyl moiety as shown in Formula (II), the (5-6 membered)heteroaryl of the (C1-C6)alkyl(5-6 membered)heteroaryl is selected from pyridinyl, pyrazolinyl and 1, 2, 4, oxadiazolyl.

In another embodiment, the compounds of Formula (I) are selected from the group consisting of compounds 4, 8a, 8b, 11, 14, 25a, 25b, 25c, 25d, 25e, 25f, 25g, 25h, 27a and 27b or a pharmaceutically acceptable salt thereof. In a useful embodiment, the compounds of Formula (I) are selected from the group consisting of compounds 4 and 11 or a pharmaceutically acceptable salt thereof.

The compounds of Formula (I) can form salts, which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like.

Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Prodrugs and solvates of the compounds of the invention are also contemplated herein. The term "prodrug", as employed herein, denotes a compound that is a drug precursor that, upon administration to a subject, undergoes chemical conversion by metabolic or chemical processes to yield a compound of Formula (I) or a salt and/or solvate thereof. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. A "hydrate" is a solvate wherein the solvent molecule(s) is/are $H_2O$.

Compounds of Formula (I), and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula (I), and of the salts, solvates and prodrugs of the compounds of Formula (I), are intended to be included in the present invention.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detection. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of Formula (I) can generally be prepared by following procedures analogous to those disclosed in the Schemes and/or in the Examples herein below, by substituting an appropriate isotopically labeled reagent for a non-isotopically labeled reagent.

Representative compounds of the invention include but are not limited to the compounds and Examples described herein.

The compounds according to the invention have pharmacological properties; in particular, the compounds of Formula (I) can inhibit gamma-secretase, and are therefore useful in the treatment or prevention of neurodegenerative diseases, e.g., Alzheimer's disease and other neurodegenerative diseases or conditions as described below.

Pharmaceutical compositions can comprise at least one compound of Formula (I) or a pharmaceutically acceptable salt thereof and at least one pharmaceutically acceptable carrier. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active compound. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa., herein incorporated by reference in its entirety.

Liquid form preparations include solutions, suspensions and emulsions. Water or water-propylene glycol solutions for parenteral injection or addition of sweeteners and opacifiers for oral solutions, suspensions and emulsions are examples. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active compound, e.g., an effective amount to achieve the desired purpose.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The quantity of active compound in a unit dose of preparation may be varied or adjusted from about 0.1 mg to about 1000 mg, preferably from about 0.1 mg to about 750 mg, more preferably from about 0.1 mg to about 500 mg, and most preferably from about 0.1 mg to about 250 mg, according to the particular application. The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.1 mg/day to about 1000 mg/day, in one to four divided doses.

As indicated above, the compounds of the invention may be useful in the treatment of Alzheimer's disease. Accordingly, in another embodiment of this invention a method of treating Alzheimer's disease is provided comprising administering to a patient in need thereof a therapeutically effective amount of at least one compound of Formula (I) or a pharmaceutically acceptable salt thereof.

In another embodiment of the method of treating Alzheimer's disease, the method comprises administering to a patient in need thereof a therapeutically effective amount of at least one compound of Formula (I) or a pharmaceutically acceptable salt thereof, and a therapeutically effective amount of at least one drug selected from the group consisting of BACE inhibitors; muscarinic antagonists; cholinesterase inhibitors; gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; GABAA inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase; anti-Abeta vaccine; APP ligands; agents that upregulate insulin cholesterol lowering agents; cholesterol absorption inhibitors; fibrates; LXR agonists; LRP mimics; nicotinic receptor agonists; H3 receptor antagonists; histone deacetylase inhibitors; hsp90 inhibitors; m1 muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux.

In another embodiment, a method of treating Alzheimer's disease is provided comprising administering a therapeutically effective amount of at least one compound of formula (I), in combination with a therapeutically effective amount of at least one cholinesterase inhibitor (such as, for example, (±)-2,3-dihydro-5,6-dimethoxy-2-[[1-(phenylmethyl)-4-piperidinyl]methyl]-1H-inden-1-one hydrochloride, i.e, donepezil hydrochloride, available as the Aricept® brand of donepezil hydrochloride), to a patient in need of treatment.

The invention also provides for a method of inhibiting the deposition of amyloid beta protein in, on or around neurological tissue, the method comprising administering to a patient in need thereof a therapeutically effective amount of at least one compound of the Formula (I) or a pharmaceutically acceptable salt thereof.

As the compounds of Formula (I) inhibit gamma secretase activity, the invention also provides for a method of inhibiting gamma secretase comprising administering to a patient in need thereof a therapeutically effective amount of at least one compound of the Formula (I) or a pharmaceutically acceptable salt thereof.

As the compounds of Formula (I) in inhibiting gamma secretase activity, inhibit amyloid beta production (Aβ40 and Aβ42 production) the invention also provides for a method of inhibiting amyloid beta production comprising administering to a patient in need thereof a therapeutically effective amount of at least one compound of the Formula (I) or a pharmaceutically acceptable salt thereof.

The compounds of Formula (I) may also be useful in treating a neurodegenerative disease or condition selected from the group consisting of Down's Syndrome, mild cognitive impairment, glaucoma, cerebral amyloid angiopathy, stroke, dementia, microgliosis, brain inflammation, traumatic brain injury and olfactory function loss. The method of treatment comprises administering to a patient in need thereof a therapeutically effective amount of at least one compound of the Formula (I) or a pharmaceutically acceptable salt thereof.

The compounds of Formula (I) or a pharmaceutically acceptable salt thereof may also be useful in treating cancers such as T-cell acute lymphoblastic leukemia, ovarian cancer, and lung cancers, e.g., non-small-cell lung carcinomas. The method of treatment of one of the aforementioned cancers comprises administering to a patient in need thereof a therapeutically effective amount of at least one compound of the Formula (I) or a pharmaceutically acceptable salt thereof.

The compounds of Formula (I) may also be useful in treating the aforementioned cancers in combination with a therapeutically effective amount of another pharmaceutically active agent, e.g., a glucocorticoid such as dexamethasone.

EXAMPLES

The invention disclosed herein is exemplified by the following preparations and examples, which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me4Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min-10% CH3CN, 5 min-95% CH3CN, 7 min-95% CH3CN, 7.5 min-10% CH3CN, 9 min-stop. The retention time and observed parent ion are given.

The following solvents, reagents, and conditions may be referred to by their abbreviations in parenthesis:
  Acetyl (Ac), i.e., CH₃C(O)—
  Butyl (Bu)
  Cyclopropyl (Pr-c)
  Dichloroethane (DCE)
  Dichloromethane (DCM)
  Diethyl ether (Et₂O)
  Diisobutylaluminum hydride (DIBAL-H)
  Dimethyl formamide (DMF)
  Ethanol (EtOH)
  Ethyl (Et)
  Ethyl acetate (EtOAc)
  High resolution mass spectrometry (HRMS)
  Lithium diisopropyl amide (LDA)
  Liquid chromatography/mass spectrometry (LCMS)
  m-Chloroperoxybenzoic acid (mCPBA)
  Mesyl (Ms), i.e., —S(O)₂CH₃
  Methanol (MeOH)
  Methyl (Me)
  Nuclear magnetic resonance spectroscopy (NMR)
  Preparative thin-layer chromatography (PTLC)
  Pyridine (Pyr)
  Room temperature (RT)
  Tert-butyldimethylsilyl (TBS)
  Tetrabutyl ammonium fluoride (TBAF)
  Tetrahydrofuran (THF)
  Trifluoroacetic acid (TFA)
  Trimethylsilyl (TMS)
  Trimethylsilyl chloride (TMSCl)
  Triethylamine (NEt₃ or Et₃N)

Experimental Methods

Unless otherwise noted, reagents and solvents were used as received from commercial suppliers. Proton nuclear magnetic resonance (NMR) spectra were obtained on Bruker AVANCE 300 or 500 MHz spectrometers. Spectral data is reported on a ppm (δ) scale relative to tetramethylsilane used as an internal standard. Coupling constants are reported in hertz.

Purification by Preparative High Pressure Liquid Chromatography (Prep. HPLC) was performed on a Waters Symmetry C18 7 µm (19×300 mm) column with solvent gradient program described in Method 1.

Method 1

| Time (min) | Flow (mL/min) | % A | % B |
| --- | --- | --- | --- |
| 0.0 | 20.0 | 90 | 10 |
| 15.0 | 20.0 | 0 | 100 |
| 18.0 | 20.0 | 0 | 100 |

A = Water with 0.025% v/v Hydrochloric Acid
B = Acetonitrile
UV Detection @ 254 nm High Pressure Liquid Chromatography (HPLC) analyses were obtained using a Waters Symmetry C18 5 µm (4.6×250 mm) column with solvent gradient programs described in Method 2.

Method 2

| Time (min) | Flow (mL/min) | % A | % B |
| --- | --- | --- | --- |
| 0.0 | 1.0 | 90 | 10 |
| 15.0 | 1.0 | 0 | 100 |
| 20.0 | 1.0 | 0 | 100 |

A = Water with 0.1% v/v Trifluoroacetic Acid
B = Acetonitrile with 0.1% v/v Trifluoroacetic Acid
UV Detection @ 254 nm Liquid Chromatography-Mass Spectroscopy (LC-MS) were obtained using a SunFire C18 5 µm (4.6×50 mm) column with solvent gradient program described in Method 3.

Method 3

| Time (min) | Flow (mL/min) | % A | % B |
| --- | --- | --- | --- |
| 0.0 | 1.0 | 90 | 10 |
| 4.0 | 1.0 | 0 | 100 |
| 6.0 | 1.0 | 0 | 100 |

A = Water with 0.05% v/v Trifluoroacetic Acid
B = Acetonitrile with 0.05% v/v Trifluoroacetic Acid
UV Detection @ 254 nm Mass Spectra were obtained on a Finnigan LCQ Duo LCMS ion trap electrospray ionization (ESI) mass spectrometer or a Waters ACQUITY UPLC LCMS ion trap atmospheric pressure chemical ionization (APCI) mass spectrometer.

Optical rotation data was obtained on a Perkin Elmer 341 polarimeter.

Compounds of Formula (I) can be prepared according to the procedure outlined in General Procedure 1.

Scheme 1

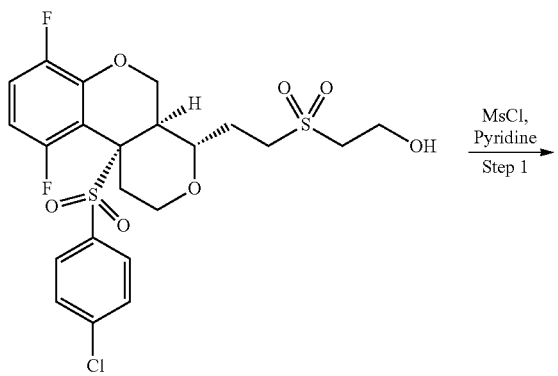

1

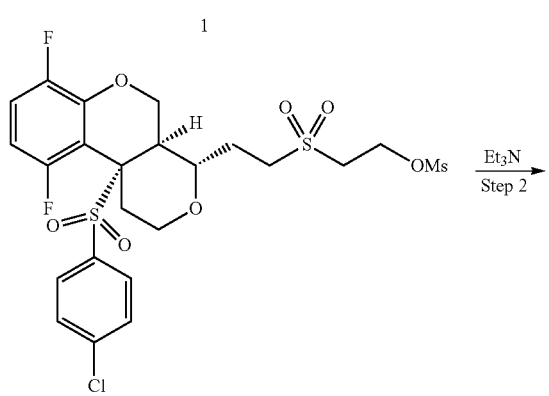

2

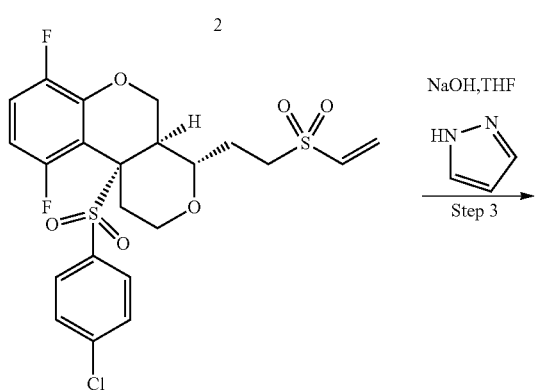

3

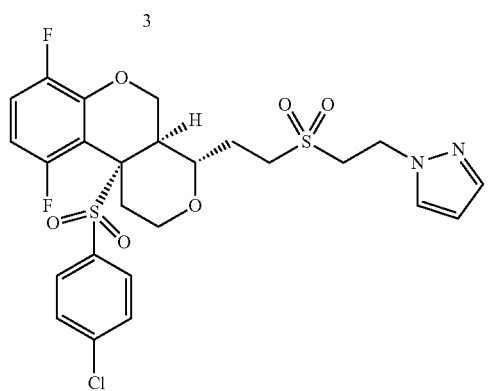

4

Scheme 2

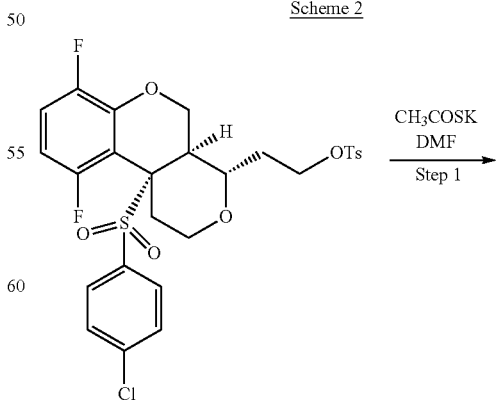

5

Step 1

To a solution of 0.4 g (0.74 mmol) of compound 1 (WO 2009/008980) in 7 mL of dichloromethane were added 0.24 g (3.0 mmol) of pyridine and 0.23 g (2.0 mmol) of methanesulfonyl chloride. The mixture was stirred at room temperature for 3 h, and concentrated. The residue was purified by chromatography eluting with 10% to 70% ethyl acetate in hexanes to give 0.38 g of compound 2. $^1$H NMR (CDCl$_3$ 400 MHz) δ 7.62 (d, J=8.8H, 2H), 7.50 (d, J=8.8 Hz, 2H), 7.10 (m, 1H), 6.44 (m, 1H), 5.16 (dd, J=12.8, 2.8 Hz, 1H), 4.61 (t, J=5.6 Hz, 2H), 4.44 (d, J=12.8 Hz, 1H), 3.86 (m, 1H), 3.35 (m, 4H), 3.10 (m, 2H), 3.05 (s, 3H), 2.55 (m, 2H), 2.43 (m, 1H), 2.28 (m, 1H), 2.02 (m, 1H). MS: Calcd. for $C_{23}H_{26}ClF_2O_9S_3$ (MH$^+$), 615.0. found 615.3. Retention time: 5.38/9 min.

Step 2

A mixture of 0.65 g (0.11 mmol) of the mesylate 2 and 0.4 g (0.4 mmol) of triethylamine in 6 mL of dichloromethane was stirred at room temperature for 18 h. The mixture was purified by chromatography eluting with 0% to 100% ethyl acetate in hexanes to give 0.56 g of compound 3. $^1$H NMR (CDCl$_3$ 400 MHz) δ 7.61 (d, J=8.4H, 2H), 7.50 (d, J=8.4 Hz, 2H), 7.08 (m, 1H), 6.60 (dd, J=16.4, 10.0 Hz, 1H), 6.45 (m, 2H), 6.18 (d, J=10 Hz, 1H), 5.15 (dd, J=12.4, 2.4 Hz, 1H), 4.40 (d, J=12.4 Hz, 1H), 3.87 (m, 1H), 2.95-3.33 (m, 4H), 3.10 (m, 3H), 2.75 (m, 4H), 2.30 (m, 2H), 1.95 (m, 1H). MS: Calcd. for $C_{22}H_{22}ClF_2O_6S_2$ (MH$^+$), 519.1. found 519.3. Retention time: 3.02/5.5 min.

Step 3

To a solution of 0.025 g (0.05 mmol) of compound 3 in 5 mL of THF were added 0.03 g (0.45 mmol) of pyrazole and trace amount of powdered NaOH. The mixture was stirred at room temperature for 1 h, and concentrated. The residue was purified by chromatography eluting with a gradient of 0 to 10% MeOH in CH$_2$Cl$_2$ plus 1% NH$_4$OH to give 0.025 g of compound 4. $^1$H NMR (CDCl$_3$ 400 MHz) δ 7.61 (d, J=8.4H, 2H), 7.60 (m, 2H), 7.49 (d, J=8.8 Hz, 2H), 7.08 (m, 1H), 6.44 (m, 1H), 6.23 (m, 1H), 5.07 (dd, J=12.8, 2.4 Hz, 1H), 4.58 (t, J=6.4 hz, 2H), 4.34 (d, J=12.8 Hz, 1H), 3.80 (m, 1H), 3.62 (m, 1H), 3.57 (m, 1H), 3.0-3.20 (m, 2H), 2.70 (m, 1H), 2.40 (m, 2H), 2.20 (m, 1H), 1.85 (m, 1H). MS: Calcd. for $C_{25}H_{26}ClF_2N_2O_6S_2$ (MH$^+$), 587.1. found 587.3. Retention time: 2.92/5.5 min.

-continued

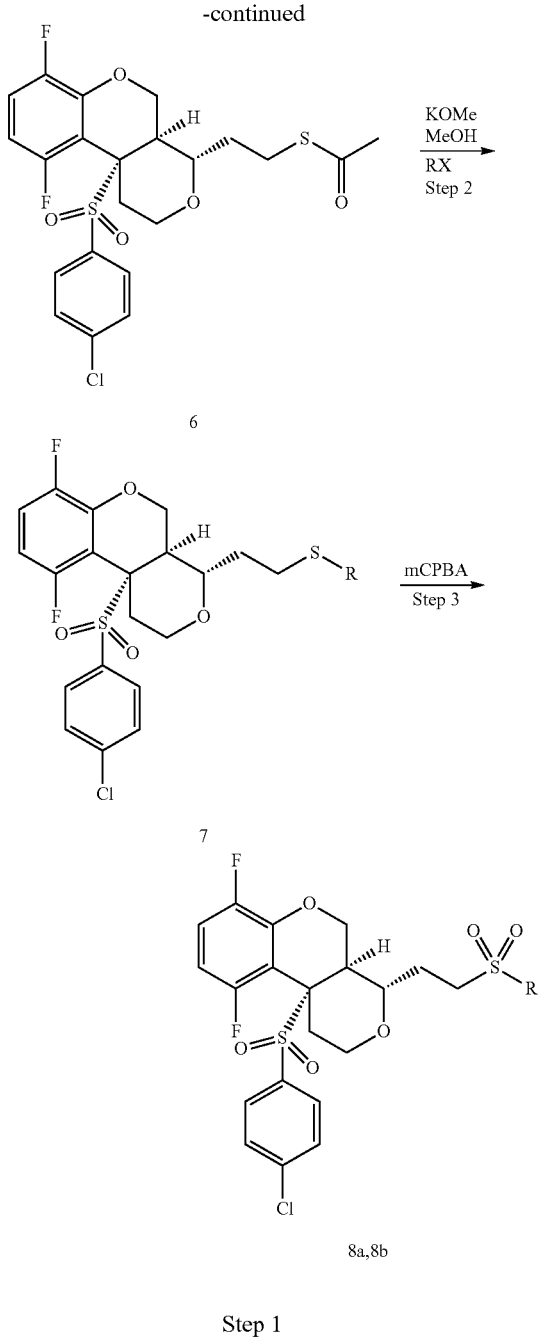

Steps 2 and 3

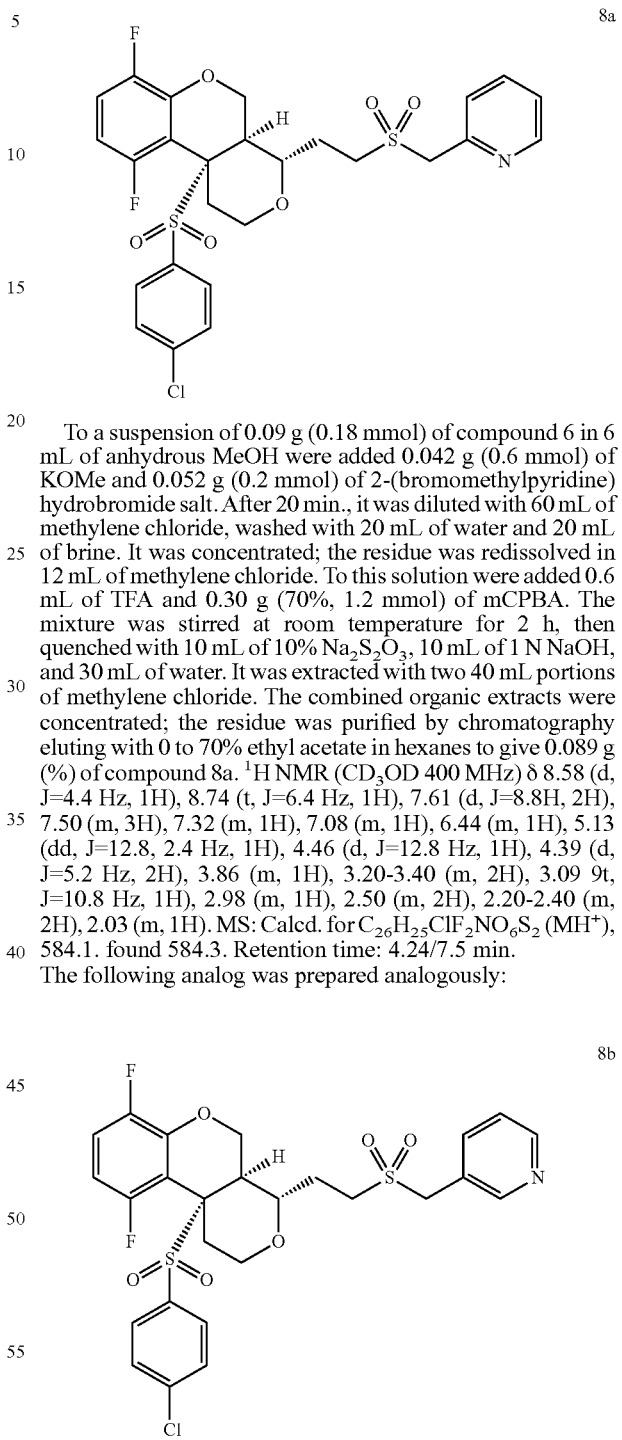

To a suspension of 0.09 g (0.18 mmol) of compound 6 in 6 mL of anhydrous MeOH were added 0.042 g (0.6 mmol) of KOMe and 0.052 g (0.2 mmol) of 2-(bromomethylpyridine) hydrobromide salt. After 20 min., it was diluted with 60 mL of methylene chloride, washed with 20 mL of water and 20 mL of brine. It was concentrated; the residue was redissolved in 12 mL of methylene chloride. To this solution were added 0.6 mL of TFA and 0.30 g (70%, 1.2 mmol) of mCPBA. The mixture was stirred at room temperature for 2 h, then quenched with 10 mL of 10% $Na_2S_2O_3$, 10 mL of 1 N NaOH, and 30 mL of water. It was extracted with two 40 mL portions of methylene chloride. The combined organic extracts were concentrated; the residue was purified by chromatography eluting with 0 to 70% ethyl acetate in hexanes to give 0.089 g (%) of compound 8a. $^1$H NMR ($CD_3OD$ 400 MHz) δ 8.58 (d, J=4.4 Hz, 1H), 8.74 (t, J=6.4 Hz, 1H), 7.61 (d, J=8.8H, 2H), 7.50 (m, 3H), 7.32 (m, 1H), 7.08 (m, 1H), 6.44 (m, 1H), 5.13 (dd, J=12.8, 2.4 Hz, 1H), 4.46 (d, J=12.8 Hz, 1H), 4.39 (d, J=5.2 Hz, 2H), 3.86 (m, 1H), 3.20-3.40 (m, 2H), 3.09 9t, J=10.8 Hz, 1H), 2.98 (m, 1H), 2.50 (m, 2H), 2.20-2.40 (m, 2H), 2.03 (m, 1H). MS: Calcd. for $C_{26}H_{25}ClF_2NO_6S_2$ ($MH^+$), 584.1. found 584.3. Retention time: 4.24/7.5 min.

The following analog was prepared analogously:

Step 1

A mixture of 1.0 g (1.6 mmol) of optically pure (−) compound 5 (WO 2009/008980) and 0.7 g (6.2 mmol) of potassium thioacetate in 10 mL of DMF was heated at 100° C. for 1.5 h, and cooled to room temperature. It was diluted with 50 mL of water, extracted with two 60 mL portions of ethyl acetate. The combined organic extracts were washed with 20 mL of brine, and concentrated. The residue was purified by $SiO_2$ chromatography eluting with 0% to 50% ethyl acetate in hexanes to give 0.78 g of compound 6. $^1$H NMR ($CD_3OD$ 400 MHz) δ7.62 (d, J=8.8H, 2H), 7.49 (d, J=8.8 Hz, 2H), 7.08 (m, 1H), 6.44 (m, 1H), 5.12 (dd, J=12.8, 2.8 Hz, 1H), 4.43 (d, J=12.8 Hz, 1H), 3.88 (dq, J=10.0, 2.0 Hz, 1H), 3.28 (m, 2H), 3.10 (m, 2H), 2.83 (m, 1H), 2.55 (m, 2H), 2.30 (s, 3H), 2.25 (m, 1H), 2.04 (m, 1H), 1.83 (m, 1H). MS: Calcd. for $C_{22}H_{22}ClF_2NO_5S_2$ ($MH^+$), 503.1. found 503.3. Retention time: 5.23/7.5 min.

$^1$H NMR ($CD_3OD$ 400 MHz) δ 8.62 (d, J=3.6 Hz, 1H), 8.56 (s, 1H), 7.80 (m, 1H), 7.61 (d, J=8.4H, 2H), 7.49 (d, J=8.4 Hz, 2H), 7.36 (m, 1H), 7.08 (m, 1H), 6.45 (m, 1H), 5.13 (dd, J=12.8, 2.8 Hz, 1H), 4.39 (d, J=12.8 Hz, 1H), 4.20 (s, 2H), 3.84 (m, 1H), 3.25 (m, 1H), 3.0-3.20 (m, 2H), 2.85 (m, 1H), 2.52 (m, 2H), 2.40 (m, 1H), 2.28 (m, 1H), 2.0 (m, 1H). MS: Calcd. for $C_{26}H_{25}ClF_2NO_6S_2$ ($MH^+$), 584.1. found 584.3. Retention time: 3.39/7.5 min.

Scheme 3

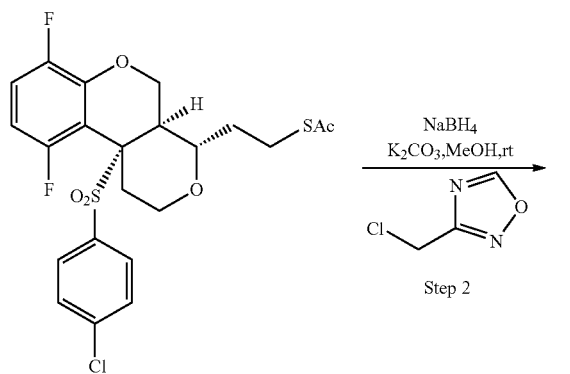

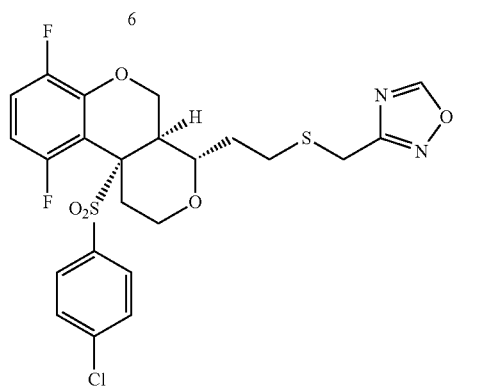

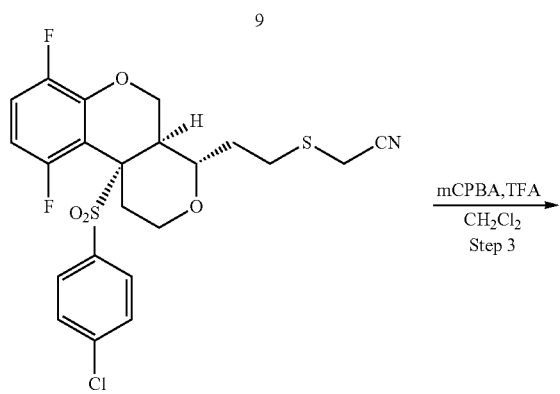

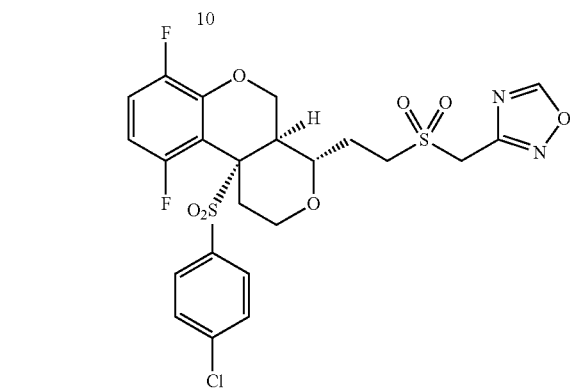

Step 1

A mixture of 0.26 g (0.516 mmol) of compound 6, 0.01 g (0.258 mmol) of sodium borohydride, and 0.142 g (1.03 mmol) of potassium carbonate in 5.2 mL of methanol was stirred at room temperature for 20 min. To the mixture was added 0.122 g (1.03 mmol) of 2-chloromethyloxadiazole and the reaction was stirred for an additional 30 min. The reaction was quenched with 10 mL of saturated aqueous ammonium chloride and extracted with three 10 mL of methylene chloride. The combined extracts were dried over anhydrous magnesium sulfate, filtered, and concentrated under reduced pressure to give 0.309 g of crude sulfide products 9 and 10, which were used directly without further purification: 9: MS Calcd. for $C_{23}H_{21}ClF_2N_2NaO_5S_2$ $(MNa)^+$, m/z=565.0. found 565.0. Retention time: 3.24 min.

10: $^1$H NMR (CD$_3$OD 400 MHz) δ 7.62 (d, J=8.8H, 2H), 7.50 (d, J=8.8 Hz, 2H), 7.08 (m, 1H), 6.46 (m, 1H), 5.15 (dd, J=12.4, 2.4 Hz, 1H), 4.41 (d, J=12.4 Hz, 1H), 3.87 (m, 1H), 3.36 (m, 4H), 3.29 (s, 2H), 3.15 (m, 1H), 2.95 (m, 1H), 2.78 (m, 1H), 2.55 (m, 2H), 2.30 (m, 1H), 2.18 (m, 1H), 1.95 (m, 1H). MS: Calcd. for $C_{22}H_{21}ClF_2NO_4S_2$ $(MH^+)$, 500.1. found 500.3. Retention time: 5.87/9.0 min.

Step 2

The crude sulfide products 9 and 10 were dissolved in 5.7 mL of methylene chloride. To the resulting solution was added 0.13 g (1.14 mmol) of trifluoroacetic acid and 0.394 g (70%, 1.59 mmol) of 3-chloroperoxybenozic acid. The reaction was stirred at room temperature for 1.5 h. After this time, the reaction was diluted with 10 mL of methylene chloride and washed with three 10 mL portions of saturated aqueous sodium bicarbonate, dried over anhydrous magnesium sulfate, filtered, and concentrated under reduced pressure. The residue was purified by column chromatography (silica, 10-60% EtOAc/heptane) to afford 0.076 g (27%) of compound 11 as a white solid: $^1$H NMR (DMSO-d$_6$ 500 MHz) δ 9.71 (s, 1H), 7.67-7.81 (m, 4H), 7.42 (td, J=9.8, 4.7 Hz, 1H), 6.76 (ddd, J=12.8, 9.2, 3.9 Hz, 1H), 4.86-5.02 (m, 3H), 4.59 (d, J=12.7 Hz, 1H), 3.84-3.99 (m, 1H), 3.38-3.49 (m, 1H), 3.25-3.36 (m, 2H), 3.05 (t, J=11.8 Hz, 1H), 2.55 (d, J=13.8 Hz, 1H), 2.41 (d, J=10.2 Hz, 1H), 2.28-2.38 (m, 1H), 2.16 (t, J=11.7 Hz, 1H), 1.92-2.06 (m, 1H). MS: Calcd. for $C_{23}H_{21}ClF_2N_2NaO_7S_2$ $(MNa)^+$, m/z=597.0. found 597.0. HPLC (Method 2) 96.1% (AUC), $t_R$=15.66 min. $[α]^{20}_D$=−129.5° (c 0.23, DMSO).

Scheme 4

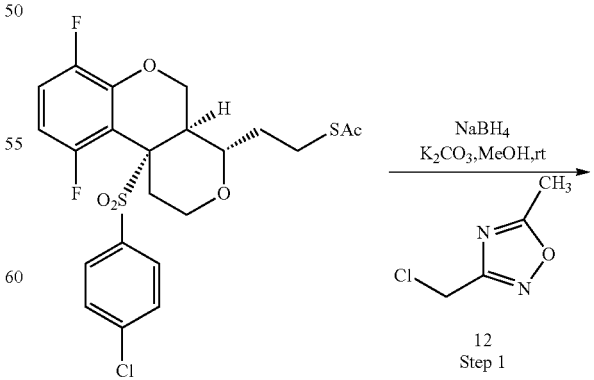

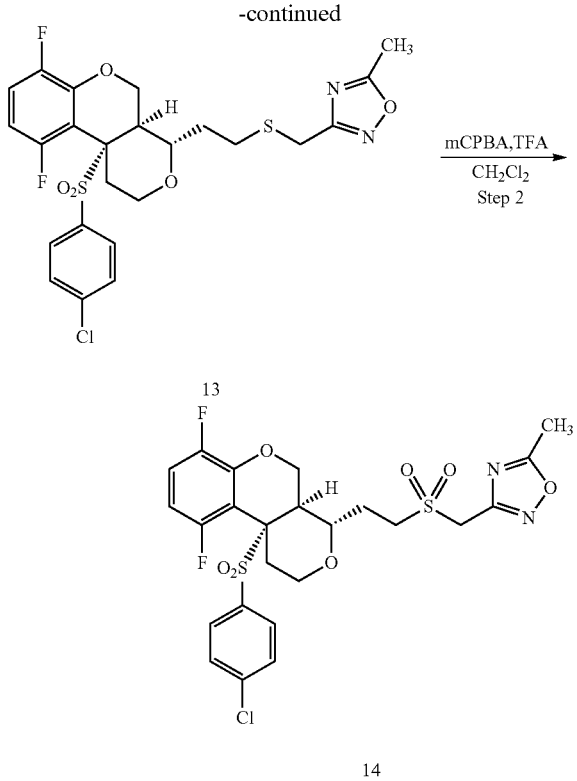

Step 1

A solution of 0.103 g (0.205 mmol) of compound 6, 0.004 g (0.10 mmol) of sodium borohydride, and 0.057 g (0.41 mmol) of potassium carbonate in 2.1 mL of methanol was stirred at room temperature for 20 min. To this solution was added 0.054 g (0.41 mmol) of compound 12, and the reaction was stirred for 1 h. After this time, the reaction was quenched with 10 mL of saturated aqueous ammonium chloride and extracted with three 10 mL of methylene chloride. The combined organics were dried over anhydrous magnesium sulfate, filtered, and concentrated to afford the crude product 13 which was used directly without further purification: MS: Calcd. for $C_{24}H_{23}ClF_2N_2NaO_5S_2$ (MNa$^+$), m/z=579.1. found 579.1. Retention time: 2.31 min.

Step 2

To a stirred solution of crude product 13 in 4 mL of methylene chloride was added 0.142 g (70%, 0.57 mmol) of 3-chloroperoxybenozic acid. The reaction was stirred at room temperature for 15 h. After this time, the reaction was diluted with 15 mL of methylene chloride and washed with three 10 mL of saturated aqueous sodium bicarbonate, dried over anhydrous magnesium sulfate, filtered, and concentrated. The residue was purified by flash chromatography (silica, 10-80% ethyl acetate/heptane) to afford 0.08 g (66% over two steps) of compound 14 as a white solid: $^1$H NMR (DMSO-d$_6$ 500 MHz) δ 7.83-7.69 (m, 4H), 7.47-7.37 (m, 1H), 6.84-6.67 (m, 1H), 4.93 (dd, J=12.8, 2.5 Hz, 1H), 4.82 (q, J=14.7 Hz, 2H), 4.60 (d, J=12.7 Hz, 1H), 3.92 (d, J=11.7 Hz, 1H), 3.48-3.36 (m, 1H), 3.35-3.21 (m, 1H), 3.05 (t, J=11.8 Hz, 1H), 2.62 (s, 3H), 2.57-2.52 (m, 1H), 2.42 (d, J=10.1 Hz, 1H), 2.39-2.26 (m, 1H), 2.17 (t, J=11.8 Hz, 1H), 2.07 (s, 1H), 2.04-1.91 (m, 1H). MS: Calcd. for $C_{24}H_{27}ClF_2N_3O_7S_2$ (MNH$_4^+$), m/z=606.1. found 606.2. HPLC (Method 2) 96.9% (AUC), $t_R$=15.92 min. $[α]^{20}_D$=−85.2° (c 0.250, DMSO).

Scheme 5

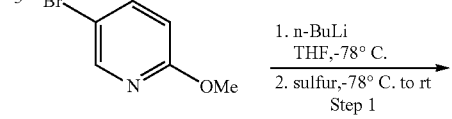

Step 1

To a stirred solution of 2.00 g (10.6 mmol) of compound 15 in 60 mL of THF at −78° C. under nitrogen was added 5.5 mL (2.5 M in hexanes, 13.8 mmol) of n-butyllithium dropwise and the mixture was stirred at this temperature for 30 min. After this time, 1.70 g (53.0 mmol) of sulfur was added and the reaction mixture was warmed to room temperature over 1 h. After this time, the reaction was quenched with 15 mL of saturated aqueous ammonium chloride and 10 mL of water and the layers were separated. The aqueous layer was extracted with four 15 mL portions of methylene chloride. The combined organics were washed with two 10 mL portions of water and 10 mL of brine, dried over anhydrous magnesium sulfate, filtered, and concentrated to afford crude 0.86 g (58%) of compound 16, which was used in the subsequent step without further purification: $^1$H NMR (CDCl$_3$ 500 MHz) δ 8.20 (s, 1H), 7.73 (m, 1H), 6.69 (d, J=5.0 Hz, 1H), 3.92 (s, 3H).

Scheme 6

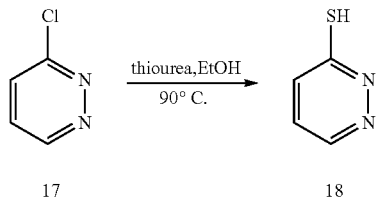

A suspension of 0.508 g (4.44 mmol) of compound 17 and 0.338 g (4.44 mmol) of thiourea in 18 mL of ethanol was heated at 90° C. for 2 h. After this time, the reaction mixture was cooled to room temperature and concentrated. To the residue was added 30 mL of water, followed by 0.235 g (2.22 mmol) of sodium carbonate and the resulting solution was extracted with four 25 mL portions of methylene chloride. The combined organics were dried over anhydrous sodium sulfate, filtered, and concentrated to afford 0.34 g (68%) of compound 18 as a dark-yellow solid: MS: Calcd. for $C_4H_5N_2S$ (MH$^+$), m/z=113.0. found 113.0. Retention time: 1.56 min.

The following compound was prepared analogously:

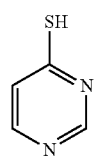

$^1$H NMR (CDCl$_3$ 500 MHz) δ 11.73 (s, 1H), 8.13 (s, 1H), 7.85 (d, J=6.2 Hz, 1H), 7.32 (dd, J=6.2, 1.0 Hz, 1H).

Scheme 7

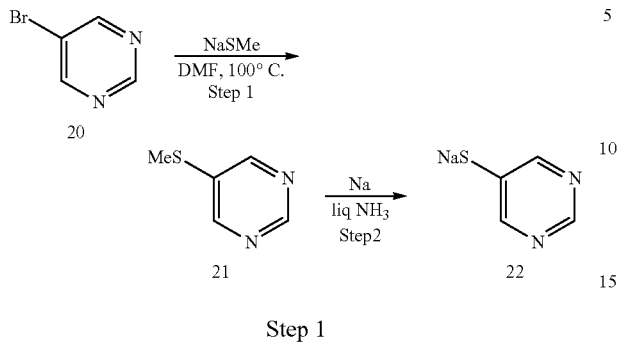

Step 1

A stirred solution of 2.00 g (12.6 mmol) of compound 20 and 1.76 g (25.2 mmol) of sodium methanethiolate in 10 mL of DMF was heated at 90° C. under nitrogen for 1 h. The reaction was cooled to room temperature and poured into 20 mL of ice water. The aqueous layer was extracted with two 20 mL portions of ethyl acetate and the combined organics were dried over anhydrous sodium sulfate, filtered, and concentrated under reduced pressure. The residue was purified by flash chromatography (silica, 0-20% ethyl acetate/hexanes) to afford 1.36 g (86%) of compound 21 as a yellow brown solid: $^1$H NMR (CDCl$_3$ 300 MHz) δ 8.99 (s, 1H), 8.62 (s, 2H), 2.54 (s, 3H). MS: Calcd. for C$_5$H$_7$N$_2$(MH$^+$), m/z=127.0. found 127.4.

Step 2

To a stirred solution of 1.36 g (10.8 mmol) of compound 21 in 50 mL of liquid ammonia condensed from ammonia gas at −78° C. under nitrogen, was added sodium metal and the reaction was stirred vigorously until the solution was blue. The solution was warmed to room temperature and stirred overnight. Liquid ammonia evaporated overnight affording a brown residue. The residue was dissolved in 50 mL of water and washed with 50 mL of diethyl ether. The aqueous layer was concentrated under reduced pressure to afford 1.40 g (99%) of compound 22 as a yellow solid: $^1$H NMR (CDCl$_3$ 500 MHz) δ 8.56 (s, 2H), 8.45 (s, 1H).

Scheme 8

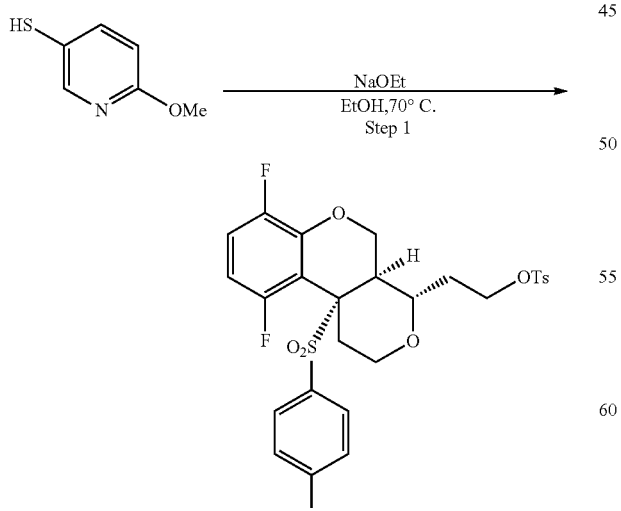

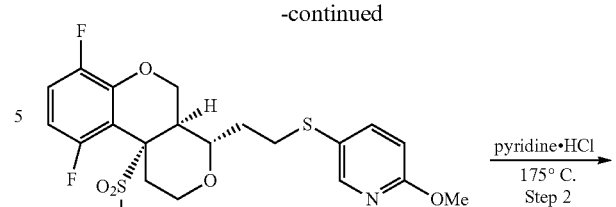

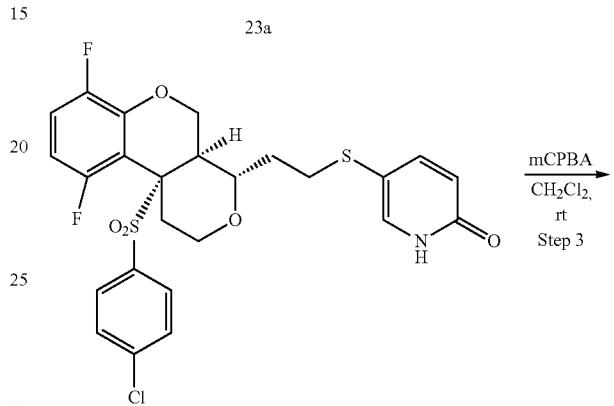

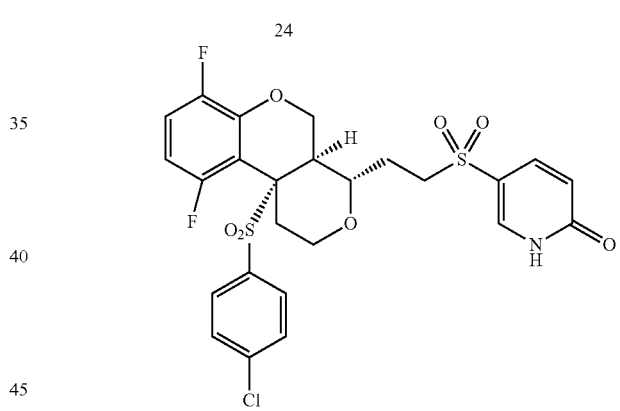

Step 1

A mixture of 0.059 g (0.417 mmol) of crude 16 and 0.048 g (2.09 mmol) of sodium ethoxide in 4.2 mL of ethanol was stirred at room temperature for 30 min. After this time, 0.25 g (0.417 mmol) of compound 5 was added and the reaction mixture was heated at 70° C. for 2 h. The reaction mixture was cooled to room temperature, concentrated, and the residue was partitioned between 50 mL of saturated aqueous ammonium chloride and 50 mL of methylene chloride. The aqueous layer was extracted with three 15 mL portions of methylene chloride. The combined organics were dried over anhydrous magnesium sulfate, filtered, and concentrated. The resulting residue was purified by column chromatography (silica, 0-30% ethyl acetate/heptane) to afford 0.166 g (70%) of compound 23a as a white solid: MS: Calcd. for C$_{26}$H$_{25}$ClF$_2$NO$_5$S$_2$ (MH$^+$), m/z=568.1. found 568.0. Retention time: 2.59 min.

The following compounds were prepared analogously:

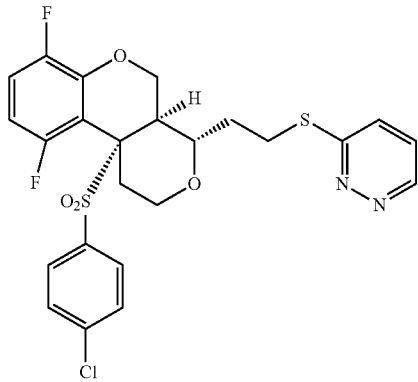

23b

MS: Calcd. for $C_{24}H_{22}ClF_2N_2O_4S_2$ (MH$^+$), m/z=539.1. found 539.1. Retention time: 2.30 min.

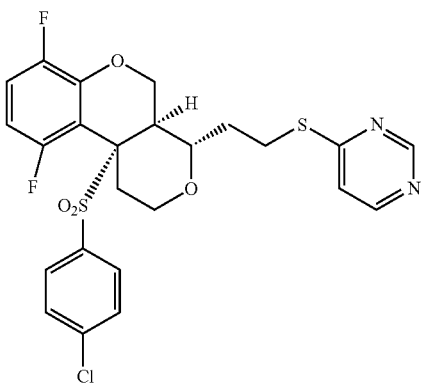

23c

MS: Calcd. for $C_{24}H_{22}ClF_2N_2O_4S_2$ (MH$^+$), m/z=539.1. found 539.0. Retention time: 2.31 min.

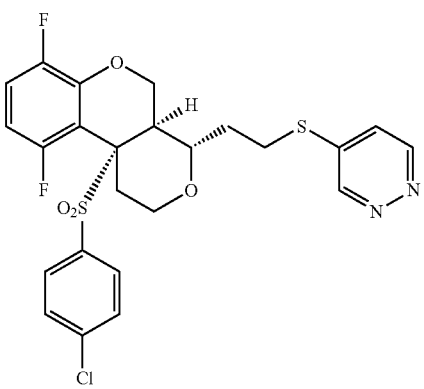

23d

MS: Calcd. for $C_{24}H_{22}ClF_2N_2O_4S_2$ (MH$^+$), m/z=539.1. found 539.1. Retention time 2.10 min.

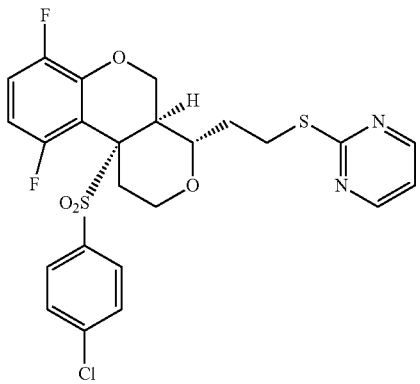

23e

MS: Calcd. for $C_{24}H_{22}ClF_2N_2O_4S_2$ (MH$^+$), m/z=539.1. found 539.0.

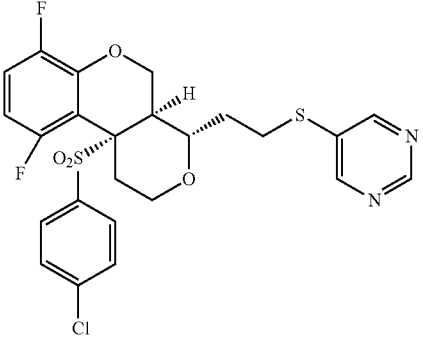

23f $^1$H NMR (CDCl$_3$ 500 MHz) δ 8.42 (d, J=1.5 Hz, 1H), 8.36-8.35 (m, 1H), 8.20 (d, J=1.5 Hz, 1H), 7.63 (d, J=8.5 Hz, 2H), 7.51 (d, J=8.5 Hz, 1H), 7.11-7.08 (m, 1H), 6.48-6.43 (m, 1H), 5.15 (dd, J=13.0, 3.0 Hz, 1H), 4.47 (d, J=12.5 Hz, 1H), 3.94-3.90 (m, 1H), 3.44-3.38 (m, 2H), 3.18-3.09 (m, 2H), 2.65-2.63 (m, 1H), 2.52 (d, J=13.5 Hz, 1H), 2.35-2.29 (m, 1H), 2.27-2.20 (m, 1H), 2.06-1.98 (m, 1H).

23g $^1$H NMR (CDCl$_3$ 500 MHz) δ 9.01 (s, 1H), 8.66 (s, 2H), 7.63 (d, J=8.5 Hz, 2H), 7.51 (d, J=8.5 Hz, 2H), 7.14-7.09 (m, 1H), 6.50-6.45 (m, 1H), 5.14 (dd, J=12.5, 2.5 Hz, 1H), 4.35 (d, J=12.5 Hz, 1H), 3.90-3.86 (m, 1H), 3.45-3.38 (m, 1H), 3.18-3.13 (m, 1H), 3.10-3.05 (m, 1H), 3.01-2.96 (m, 1H), 2.56 (d, J=10.5 Hz, 1H), 2.51 (d, J=10.5 Hz, 1H), 2.32-2.25 (m, 1H), 2.19-2.12 (m, 1H), 1.93-1.86 (m, 1H).

Step 2

A mixture of 0.166 g (0.292 mmol) of compound 23a and 0.034 g (0.292 mmol) of pyridine hydrochloride was heated at 175° C. for 10 min. After this time, the reaction mixture was cooled to room temperature, diluted with 5 mL of 1 N hydrochloric acid and 10 mL of methylene chloride, and the layers were separated. The aqueous layer was extracted with three 15 mL portions of methylene chloride. The combined organics were washed with two 10 mL portions of water and 10 mL of brine, dried over anhydrous magnesium sulfate, filtered, and concentrated. The residue was purified by flash chromatography (silica, 0-40% ethyl acetate/heptane) to afford 0.111 g (68%) of compound 24 as a white solid: MS: Calcd. for $C_{25}H_{23}ClF_2NO_5S_2$ (MH$^+$), m/z=554.1. found 554.1. Retention time: 2.07 min.

Step 3

To a solution of 0.111 g (0.20 mmol) of compound 24 in 2 mL of methylene chloride was added 0.173 g (70%, 0.7 mmol) of 3-chloroperbenzoic acid (mCPBA) and the mixture was stirred at room temperature for 3 h. After this time, the reaction was quenched with 20 mL of saturated aqueous sodium bicarbonate. The layers were separated and the aqueous layer was extracted with three 15 mL portions of methylene chloride. The combined organics were dried over anhydrous magnesium sulfate, filtered, and concentrated. The residue was purified by flash chromatography (silica, 0-40% methanol/methylene chloride) to afford 0.058 g (50%) of compound 25a as a white solid: $^1$H NMR (DMSO-d$_6$ 300 MHz) δ 12.36 (s, 1H), 7.91 (d, J=2.6 Hz, 1H), 7.82-7.58 (m, 5H), 7.49-7.33 (m, 1H), 6.83-6.67 (m, 1H), 6.43 (d, J=9.7 Hz, 1H), 4.96-4.82 (m, 1H), 4.50 (d, J=12.8 Hz, 1H), 3.86 (d, J=11.6 Hz, 1H), 3.42-3.13 (m, 3H), 2.97 (t, J=11.8 Hz, 1H), 2.48-2.32 (m, 2H), 2.24-2.09 (m, 2H), 1.89-1.71 (m, 1H). MS: Calcd. for $C_{25}H_{23}ClF_2NO_7S_2$ (MH$^+$) m/z=586.1. found 586.0. Retention time: 2.73 min. HPLC (Method 2) 97.5% (AUC), t$_R$=13.86 min.

The following compounds were prepared analogously according to Scheme 4, step 2:

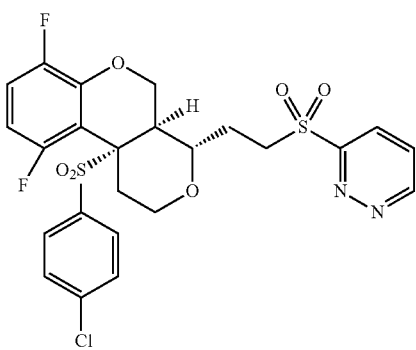

25b $^1$H NMR (DMSO-d$_6$ 500 MHz) δ 9.52 (dd, J=5.1, 1.3 Hz, 1H), 8.29 (dd, J=8.5, 1.3 Hz, 1H), 8.17-8.00 (m, 1H), 7.75-7.70 (m, 4H), 7.41 (td, J=9.8, 4.6 Hz, 1H), 6.85-6.66 (m, 1H), 4.87 (dd, J=12.8, 2.3 Hz, 1H), 4.46 (d, J=12.8 Hz, 1H), 3.84 (d, J=12.0 Hz, 1H), 3.79-3.59 (m, 2H), 3.22 (td, J=9.8, 2.2 Hz, 1H), 2.93 (t, J=11.9 Hz, 1H), 2.37 (d, J=10.1 Hz, 1H), 2.33-2.17 (m, 1H), 2.17-2.01 (m, 2H), 1.97-1.83 (m, 1H). MS: Calcd. for $C_{24}H_{21}ClF_2N_2NaO_6S_2$ (MNa$^+$) m/z=593.0. found 593.1. Retention time: 2.96 min. HPLC (Method 2)>99% (AUC), t$_R$=18.16 min. [α]$^{20}_D$=−54.6° (c 0.150, DMSO).

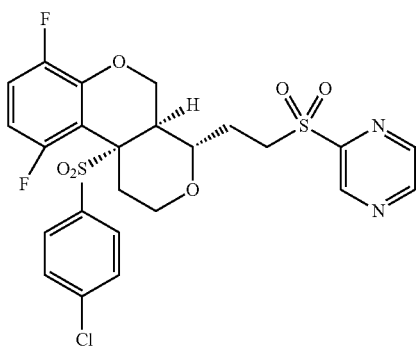

25c $^1$H NMR (CDCl$_3$ 500 MHz) δ 9.39 (d, J=1.2 Hz, 1H), 9.12 (d, J=5.0 Hz, 1H), 8.01 (dd, J=5.0, 1.3 Hz, 1H), 7.62 (d, J=8.6 Hz, 2H), 7.53-7.47 (m, 2H), 7.11 (td, J=9.4, 4.7 Hz, 1H), 6.50-6.38 (m, 1H), 5.15 (dd, J=12.7, 2.6 Hz, 1H), 4.37 (d, J=12.7 Hz, 1H), 3.89-3.78 (m, 1H), 3.76-3.64 (m, 1H), 3.55-3.39 (m, 1H), 3.32 (td, J=9.7, 2.8 Hz, 1H), 3.08 (t, J=11.7 Hz, 1H), 2.56-2.49 (m, 1H), 2.46-2.35 (m, 1H), 2.27 (dd, J=16.8, 7.3 Hz, 1H), 2.10-1.98 (m, 1H). MS: Calcd. for $C_{24}H_{22}ClF_2N_2O_6S_2$ (MH), m/z=571.0. found 571.2. HPLC (Method 2) 99.0% (AUC), t$_R$=15.71 min. [α]$^{23}_D$=−91.3° (c 0.230, Acetonitrile).

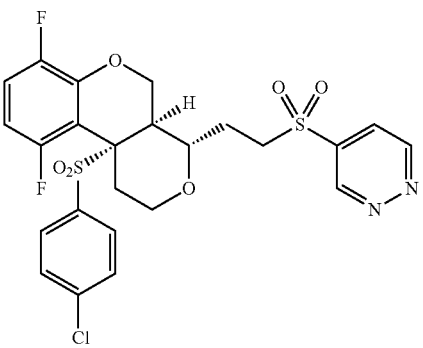

25d $^1$H NMR (CDCl$_3$ 500 MHz) δ 9.60 (s, 1H), 9.56 (d, J=5.2 Hz, 1H), 7.91 (dd, J=5.2, 2.3 Hz, 1H), 7.61 (d, J=8.5 Hz, 2H), 7.51 (d, J=8.7 Hz, 2H), 7.12 (td, J=9.4, 4.7 Hz, 1H), 6.51-6.35 (m, 1H), 5.17 (dd, J=12.7, 2.4 Hz, 1H), 4.37 (d, J=12.6 Hz, 1H), 3.89-3.70 (m, 1H), 3.48-3.33 (m, 1H), 3.33-3.18 (m, 2H), 3.00 (t, J=11.9 Hz, 1H), 2.50 (m, 2H), 2.45-2.33 (m, 1H), 2.24 (t, J=12.0 Hz, 1H), 2.03-1.82 (m, 1H). MS: Calcd. for $C_{24}H_{22}ClF_2N_2O_6S_2$ (MH$^+$), m/z=571.1. found 571.2. HPLC (Method 2) 97.2% (AUC), t$_R$=15.19 min. [α]$^{23}_D$=−137.0° (c 0.150, Chloroform).

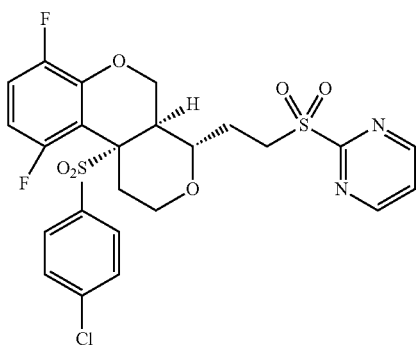

25e $^1$H NMR (CDCl$_3$ 500 MHz) δ 8.96 (d, J=5.0 Hz, 2H), 7.62 (d, J=8.5 Hz, 2H), 7.58 (t, J=5.0 Hz, 1H), 7.51 (d, J=8.5 Hz,

2H), 7.13-7.08 (m, 1H), 6.49-6.45 (m, 1H), 5.14 (dd, J=12.5, 3.0 Hz, 1H), 4.39 (d, J=11.0 Hz, 1H), 3.89-3.78 (m, 2H), 3.55-3.49 (m, 1H), 3.40-3.35 (m, 1H), 3.12 (t, J=11.5 Hz, 1H), 2.57-2.46 (m, 3H), 2.46-2.31 (m, 1H), 2.14-2.10 (m, 1H). MS: Calcd. for $C_{24}H_{21}ClF_2N_2NaO_6S_2$ (MNa$^+$), m/z=593.0. found 593.3. Retention time: 3.00 min. HPLC (Method 2) 95.7% (AUC), $t_R$=15.53 min. $[\alpha]^{25}_D$=−197.0° (c 0.120, Methylene Chloride).

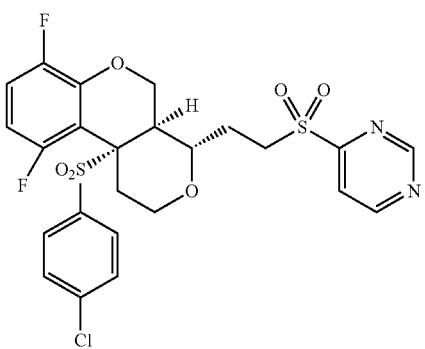

25f $^1$H NMR (CDCl$_3$ 500 MHz) δ 9.29 (d, J=1.0 Hz, 1H), 8.88 (d, J=2.0 Hz, 1H), 8.73-8.72 (m, 1H), 7.61 (d, J=8.5 Hz, 2H), 7.50 (d, J=8.5 Hz, 2H), 7.12-7.08 (m, 1H), 6.49-6.46 (m, 1H), 5.14 (dd, J=13.0, 3.0 Hz, 1H), 4.37 (d, J=12.5 Hz, 1H), 3.86-3.82 (m, 1H), 3.69-3.63 (m, 1H), 3.44-3.38 (m, 1H), 3.34-3.29 (m, 1H), 3.10-3.05 (m, 1H), 2.55-2.49 (m, 2H), 2.45-2.38 (m, 1H), 2.29-2.23 (m, 1H), 2.06-1.99 (m, 1H). MS: Calcd. for $C_{24}H_{21}ClF_2N_2NaO_6S_2$ (MNa$^+$), m/z=593.0. found 593.0. Retention time: 3.00 min. HPLC (Method 2)>99% (AUC), $t_R$=15.86 min. $[\alpha]^{20}_D$=−134.0° (c 0.100, Methylene Chloride).

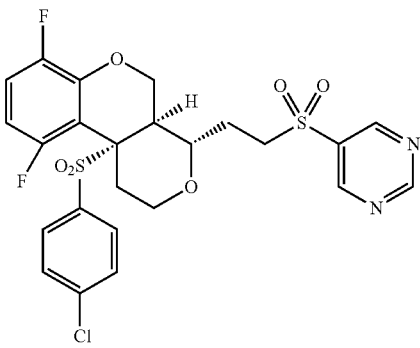

25g $^1$H NMR (CDCl$_3$ 500 MHz) δ 9.46 (s, 1H), 9.18 (s, 2H), 7.61 (d, J=8.5 Hz, 2H), 7.51 (d, J=8.5 Hz, 2H), 7.13-7.09 (m, 1H), 6.49-6.44 (m, 1H), 5.17 (dd, J=12.5, 2.5 Hz, 1H), 4.38 (d, J=12.5 Hz, 1H), 3.84-3.80 (m, 1H), 3.45-3.39 (m, 1H), 3.30-3.19 (m, 2H), 3.06-3.02 (m, 1H), 2.54-2.46 (m, 2H), 2.44-2.37 (m, 1H), 2.28-2.21 (m, 1H), 2.01-1.93 (m, 1H). MS: Calcd. for $C_{24}H_{21}ClF_2N_2NaO_6S_2$ (MNa$^+$), m/z=593.0. found 592.9. Retention time: 3.03 min. HPLC (Method 2)>99% (AUC), $t_R$=18.28 min. $[\alpha]^{20}_D$=−169.0° (c 0.100, Methylene Chloride).

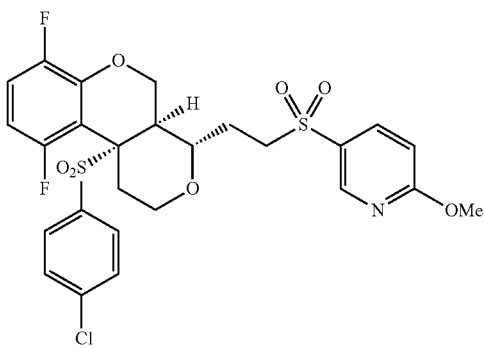

25h $^1$H NMR (CDCl$_3$ 500 MHz) δ 8.67 (d, J=2.4 Hz, 1H), 7.97 (dd, J=8.8, 2.5 Hz, 1H), 7.62 (d, J=8.5 Hz, 2H), 7.51 (d, J=8.7 Hz, 2H), 7.11 (td, J=9.4, 4.7 Hz, 1H), 6.86 (d, J=8.8 Hz, 1H), 6.54-6.36 (m, 1H), 5.14 (dd, J=12.7, 2.5 Hz, 1H), 4.37 (d, J=12.6 Hz, 1H), 4.03 (s, 3H), 3.90-3.78 (m, 1H), 3.39-3.21 (m, 2H), 3.21-3.10 (m, 1H), 3.05 (t, J=11.8 Hz, 1H), 2.58-2.44 (m, 2H), 2.44-2.29 (m, 1H), 2.29-2.17 (m, 1H), 1.99-1.82 (m, 1H). MS: Calcd. for $C_{26}H_{25}ClF_2NO_7S_2$ (MH$^+$), m/z=600.1. found 600.1. HPLC (Method 2)>99% (AUC), $t_R$=16.93 min. $[\alpha]^{23}_D$=−67.8° (c 0.150, Acetonitrile).

Scheme 9

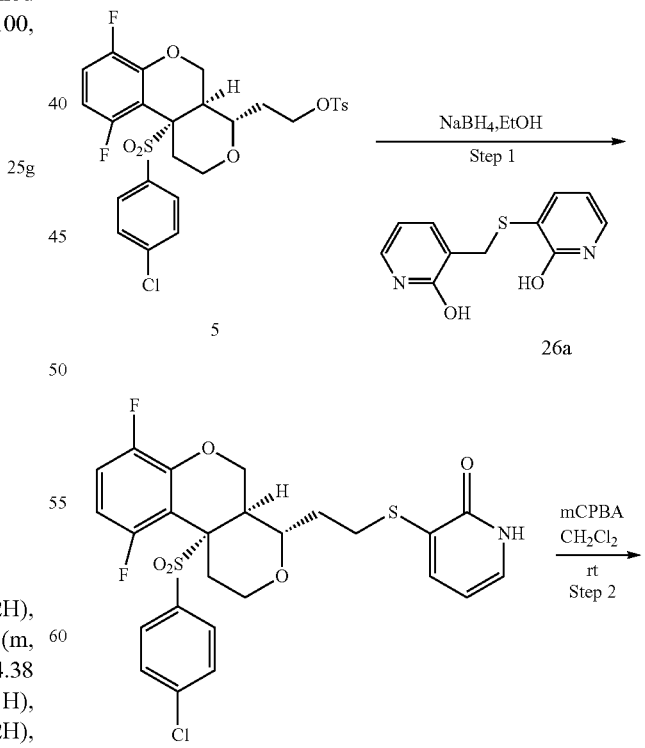

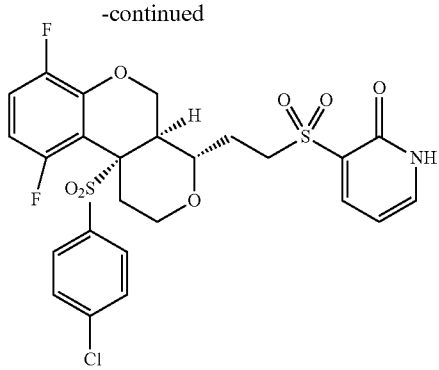

27a

Step 1

To a stirred solution of 0.050 g (0.20 mmol) of 3,3'-disulfanediyldipyridin-2-ol[1] in 5 mL of ethanol was added 0.011 g (0.30 mmol) of sodium borohydride. The reaction mixture stirred at room temperature for 20 min. To the solution, 0.108 g (0.18 mmol) of compound 5 was added and the reaction was heated at reflux for 5 h. The reaction mixture was concentrated under reduced pressure. The residue was dissolved in 20 mL of 1 N hydrochloric acid and extracted with three 15 mL of ethyl acetate. The combined organics were dried over anhydrous sodium sulfate, filtered, and concentrated. The residue was purified by flash chromatography (silica, 0-15% methanol/methylene chloride) to afford 0.075 g (67%) of compound 26a as an off-white solid: MS: Calcd. for $C_{25}H_{23}ClF_2NO_5S_2$ (MH+), m/z=554.1. found 554.3. Retention time: 2.91 min.

Note 1: The preparation of 3,3'-disulfanediyldipyridin-2-ol was previously described; see Smith, K.; Anderson, D.; Matthews, I.; *J. Org. Chem.* 1996, 61, 662.

The following compound was prepared analogously:

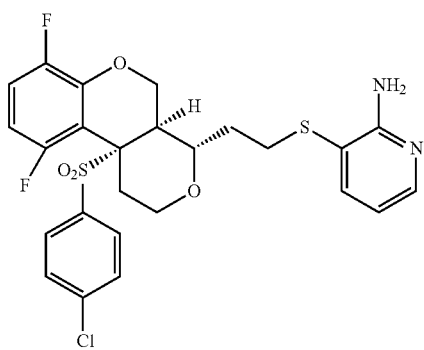

26b

26b[1]: MS: Calcd. for $C_{25}H_{24}ClF_2N_2O_4S_2$ (MH+), m/z=553.1. found 553.0. Retention time: 2.27 min.

Note 1: The preparation of 3,3'-disulfanediyldipyridin-2-amine was previously described; see Smith, K.; Anderson, D.; Matthews, I.; *J. Org. Chem.* 1996, 61, 662.

Step 2

To a stirred solution of 0.075 g (0.14 mmol) of compound 26a in 5 mL of methylene chloride was added 0.093 g (0.38 mmol) of 3-chloroperbenzoic acid. The reaction was stirred at room temperature for 3 h. After this time, the reaction mixture was diluted with 20 mL of methylene chloride and washed with 20 mL of saturated aqueous sodium bicarbonate. The aqueous layer was separated and extracted with three 20 mL portions of methylene chloride. The combined organics were dried over anhydrous sodium sulfate, filtered, and concentrated. The residue was purified by flash chromatography (silica, 0-20% methanol/methylene chloride) to afford 0.055 g (67%) of compound 27a as an off-white solid: $^1$H NMR (CD$_3$OD 300 MHz) δ 8.19 (dd, J=7.3, 2.2 Hz, 1H), 7.79-7.57 (m, 5H), 7.29-7.16 (m, 1H), 6.64-6.51 (m, 1H), 6.48 (dd, J=7.2, 6.4 Hz, 1H), 5.05 (dd, J=12.8, 2.6 Hz, 1H), 4.41 (d, J=12.3 Hz, 1H), 3.93-3.76 (m, 1H), 3.58 (t, J=7.4 Hz, 2H), 3.26 (dd, J=9.9, 2.9 Hz, 1H), 3.03 (t, J=11.9 Hz, 1H), 2.56 (d, J=13.6 Hz, 1H), 2.44 (d, J=10.3 Hz, 1H), 2.37-2.17 (m, 2H), 1.96-1.79 (m, 1H). MS: Calcd. for $C_{25}H_{22}ClF_2NNaO_7S_2$ (MNa+), m/z=608.0. found 608.5. Retention time: 2.78 min. HPLC (Method 2)>99% (AUC), $t_R$=13.91 min. $[α]^{25}_D$=−144.0° (c 0.100, Methylene Chloride).

The following compound was prepared analogously:

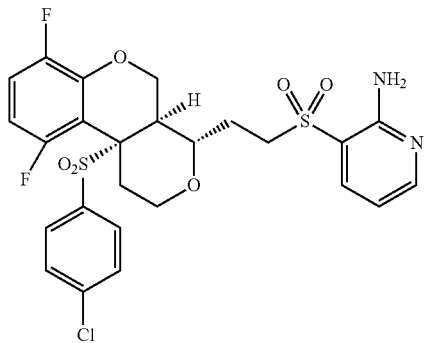

27b $^1$H NMR (CDCl$_3$ 300 MHz) δ 8.26 (dd, J=4.9, 1.8 Hz, 1H), 7.96 (dd, J=7.8, 1.8 Hz, 1H), 7.62 (d, J=8.7 Hz, 2H), 7.51 (d, J=8.8 Hz, 2H), 7.18-7.02 (m, 1H), 6.79 (dd, J=7.8, 4.9 Hz, 1H), 6.54-6.40 (m, 1H), 5.86 (s, 2H), 5.14 (dd, J=12.7, 2.6 Hz, 1H), 4.36 (d, J=12.7 Hz, 1H), 3.94-3.78 (m, 1H), 3.47-3.12 (m, 3H), 3.03 (t, J=11.5 Hz, 1H), 2.59-2.43 (m, 2H), 2.43-2.13 (m, 2H), 2.05-1.81 (m, 1H). MS: Calcd. for $C_{25}H_{24}ClF_2N_2O_6S_2$ (MH+), m/z=585.1. found 585.0. Retention time: 2.90 min. HPLC (Method 2)>99% (AUC), $t_R$=13.93 min. $[α]^{25}_D$=−156.0° (c 0.100, Methylene Chloride)

Assay

The pharmacological properties of the compounds of this invention may be evaluated by a number of pharmacological assays. The exemplified pharmacological assays, which are described later, have been carried out with the compounds according to the present invention, as well as with salts thereof.

Gamma-secretase activity was determined as described by Zhang et al. (Biochemistry, 40 (16), 5049-5055, 2001), which is herein incorporated by reference. Activity is expressed either as a percent inhibition or as the concentration of compound producing 50% inhibition of enzyme activity.

Reagents

Antibodies W02, G2-10, and G2-11 were obtained from Dr. Konrad Beyreuther (University of Heidelberg, Heidelberg, Germany). W02 recognizes residues 5-8 of Aβ peptide, while G2-10 and G2-11 recognize the specific C-terminal structure of Aβ 40 and Aβ 42, respectively. Biotin-4G8 was purchased from Senetec (St. Louis, Mo.). All tissue culture reagents used in this work were from Life Technologies, Inc., unless otherwise specified. Pepstatin A was purchased from Roche Molecular Biochemicals; DFK167 was from Enzyme Systems Products (Livermore, Calif.).

cDNA Constructs, Tissue Culture, and Cell Line Construction

The construct SPC99-Ion, which contains the first 18 residues and the C-terminal 99 amino acids of APP carrying the London mutation, has been described (Zhang, L., Song, L., and Parker, E. (1999) J. Biol. Chem. 274, 8966-8972). Upon insertion into the membrane, the 17 amino acid signal peptide is processed, leaving an additional leucine at the N-terminus of Aβ. SPC99-lon was cloned into the pcDNA4/TO vector (Invitrogen) and transfected into 293 cells stably transfected with pcDNA6/TR, which is provided in the T-REx system (Invitrogen). The transfected cells were selected in Dulbecco's modified Eagle's media (DMEM) supplemented with 10% fetal bovine serum, 100 units/mL penicillin, 100 g/mL streptomycin, 250 g/mL zeocin, and 5 g/mL blasticidin (Invitrogen). Colonies were screened for Aβ production by inducing C99 expression with 0.1 g/mL tetracycline for 16-20 h and analyzing conditioned media with a sandwich immunoassay (see below). One of the clones, designated as pTRE.15, was used in these studies.

Membrane Preparation

C99 expression in cells was induced with 0.1 g/mL tetracycline for 20 h. The cells were pretreated with 1 M phorbol 12-myristate 13-acetate (PMA) and 1 M brefeldin A (BFA) for 5-6 h at 37 C before harvesting. The cells were washed 3 times with cold phosphate-buffered saline (PBS) and harvested in buffer A containing 20 mM Hepes (pH 7.5), 250 mM sucrose, 50 mM KCl, 2 mM EDTA, 2 mM EGTA, and Complete protease inhibitor tablets (Roche Molecular Biochemicals). The cell pellets were flash-frozen in liquid nitrogen and stored at −70° C. before use.

To make membranes, the cells were resuspended in buffer A and lysed in a nitrogen bomb at 600 psi. The cell lysate was centrifuged at 1500 g for 10 min to remove nuclei and large cell debris. The supernatant was centrifuged at 100000 g for 1 h. The membrane pellet was resuspended in buffer A plus 0.5 M NaCl, and the membranes were collected by centrifugation at 200000 g for 1 h. The salt-washed membrane pellet was washed again in buffer A and centrifuged at 100000 g for 1 h. The final membrane pellet was resuspended in a small volume of buffer A using a Teflon-glass homogenizer. The protein concentration was determined, and membrane aliquots were flash-frozen in liquid nitrogen and stored at −70° C.

γ-Secretase Reaction and Aβ Analysis

To measure γ-secretase activity, membranes were incubated at 37° C. for 1 h in 50 μL of buffer containing 20 mM Hepes (pH 7.0) and 2 mM EDTA. At the end of the incubation, Aβ 40 and Aβ 42 were measured using an electrochemiluminescence (ECL)-based immunoassay. Aβ 40 was identified with antibody pairs TAG-G2-10 and biotin-W02, while Aβ 42 was identified with TAG-G2-11 and biotin-4G8. The ECL signal was measured using an ECL-M8 instrument (IGEN International, Inc.) according to the manufacturer's instructions. The data presented were the means of the duplicate or triplicate measurements in each experiment. The characteristics of γ-secretase activity described were confirmed using more than five independent membrane preparations.

As shown below in the Table, the compounds of the invention had a membrane $IC_{50}$ in the range of 1 nM to 20 nM.

TABLE

| Compound | R | $A\beta_{40}$ $IC_{50}$ (nM) |
|---|---|---|
| 4 | (propyl-pyrazolyl) | 1.4 |
| 8a | (methyl-2-pyridyl) | 1.9 |
| 8b | (methyl-3-pyridyl) | 6.6 |
| 11 | (methyl-1,2,4-oxadiazolyl) | 1.7 |
| 14 | (methyl-5-methyl-1,2,4-oxadiazolyl) | 5.8 |
| 25a | (5-pyridin-2(1H)-onyl) | 18.7 |
| 25b | (3-pyridazinyl) | 4.5 |

TABLE-continued

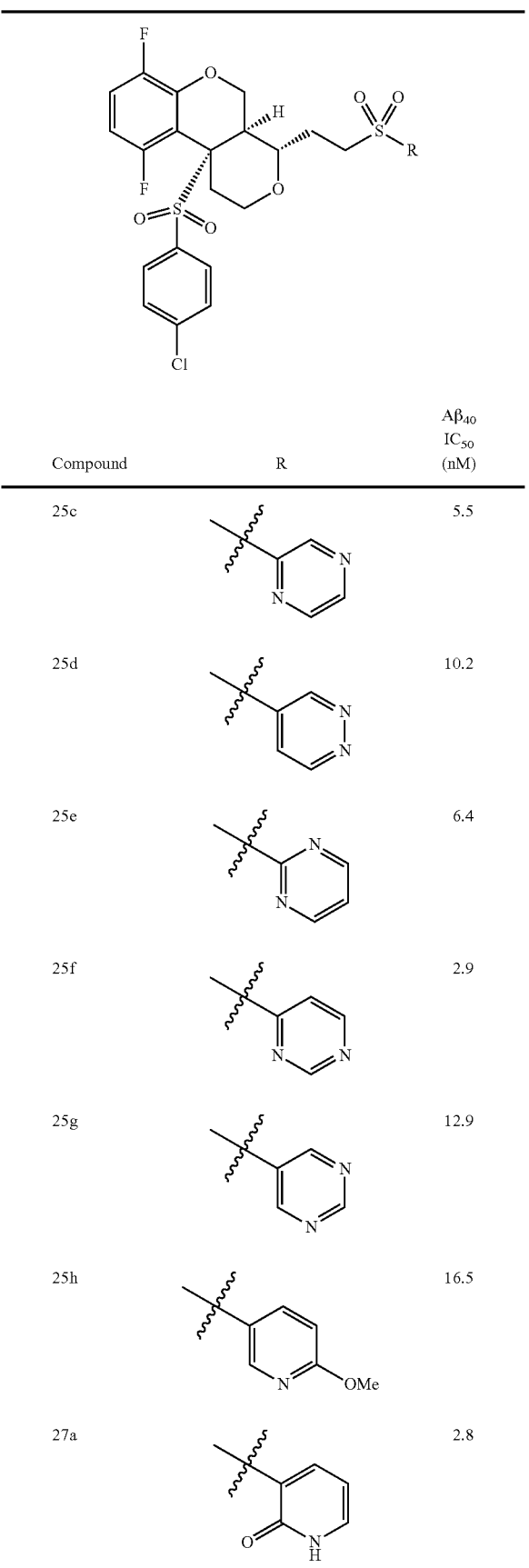

| Compound | R | Aβ40 IC50 (nM) |
|---|---|---|
| 25c | (pyrazin-2-yl with methyl) | 5.5 |
| 25d | (pyridazin-4-yl with methyl) | 10.2 |
| 25e | (pyrimidin-2-yl with methyl) | 6.4 |
| 25f | (pyrimidin-4-yl with methyl) | 2.9 |
| 25g | (pyrimidin-5-yl with methyl) | 12.9 |
| 25h | (6-methoxypyridin-3-yl with methyl) | 16.5 |
| 27a | (2-oxo-1,2-dihydropyridin-3-yl with methyl) | 2.8 |

TABLE-continued

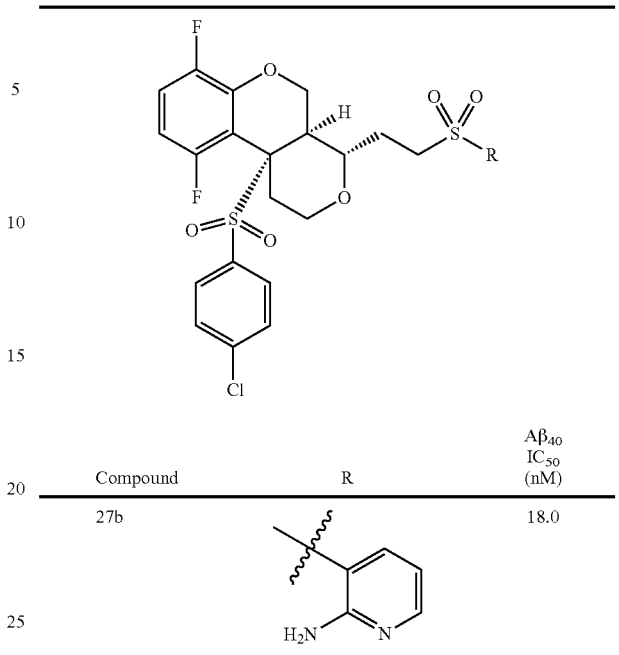

| Compound | R | Aβ40 IC50 (nM) |
|---|---|---|
| 27b | (2-aminopyridin-3-yl with methyl) | 18.0 |

While the present invention has been described in conjunction with the specific embodiments set forth above, many alternatives, modification and variations thereof will be apparent to those of ordinary skill in the art. All such alternatives, modifications and variations are intended to fall within the spirit and scope of the present invention.

What is claimed:

1. A compound of Formula (I)

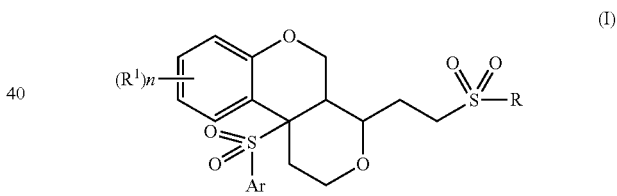

(I)

or a pharmaceutically acceptable salt thereof, wherein
R is selected from the group consisting of:
(1) -pyridinyl,
(2) -pyrazolinyl,
(3) -1,2,4-oxadiazolyl,
(4) -(C1-C2)alkyl-pyridinyl,
(5) -(C1-C2)alkyl-pyrazolinyl, and
(6) -(C1-C2)alkyl-1,2,4-oxadiazolyl,
wherein the pyridinyl, pyrazolinyl, and -1,2,4-oxadiazolyl, is unsubstituted or substited with one $L^1$ group;
$R^1$ is independently selected from the group consisting halogen, (C1-C6)alkyl, —CN, —CF$_3$, —O—(C1-C6)alkyl, —O-(halo(C1-C6)alkyl), —C(O)—O—(C1-C6)—OH-substituted (C1-C4)alkyl, halo(C1-C6)alkyl, —(C1-C4)alkoxy-OH, —(C1-C4)alkoxy(C1-C4)alkoxy and —S(O)$_2$(C1-C6)alkyl;
n is 0, 1, 2, or 3;
Ar is selected from the group consisting of phenyl optionally substituted with 1 or 2 $L^2$ groups, and pyridyl optionally substituted with 1 or 2 $L^2$ groups;
$L^1$ is independently selected from the group consisting of —OCH$_3$, —NH$_2$, =O, and (C1-C5)alkyl; and
$L^2$ is independently selected from the group consisting of halogen, (C1-C6)alkyl , —CN, —CF$_3$, —O—(C1-C6)

alkyl, —O-(halo(C1-C6)alkyl), —C(O)—O—(C1-C6) alkyl, —OH-substituted(C1-C6)alkyl, halo(C1-C6) alkyl, —OH-substituted (C1-C4)alkoxy, —(C1-C4) alkoxy(C1-C4)alkoxy and —S(O)₂(C1-C6)alkyl.

2. The compound of claim 1, wherein n is 2, each R¹ is the same or different halogen, and the R¹ groups are bound to the phenyl moiety as shown in Formula (II):

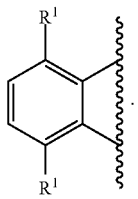

II

3. The compound of claim 2, wherein the halogen is fluoro.

4. The compound of claim 1, wherein Ar is selected from the group consisting of p-Cl-phenyl-, p-CN-phenyl-, p-CF₃-phenyl, pyridyl, and pyridyl substituted with 1 or 2 substituents independently selected from the group consisting of halogen, —(C1-C6)alkyl, —CN, —CF₃, O—(C1-C6)alkyl, —O-halo(C1-C6)alkyl, —C(O)—O—(C1-C6)alkyl, —OH-substituted (C1-C6)alkyl, - -halo(C1-C6)alkyl, -OH substituted (C1-C4)alkoxy and —(C1-C4)alkoxy(C1-C4)alkoxy.

5. The compound of claim 4, wherein Ar is p-Cl-phenyl.

6. The compound of claim 1, having the Formula:

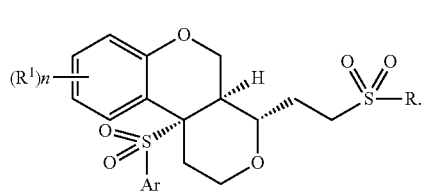

(IA)

7. The compound of claim 6, wherein Ar is p-Cl-phenyl, n is 2, each R¹ is the same or different halogen, and the R¹ groups are bound to the phenyl moiety as shown in Formula (II):

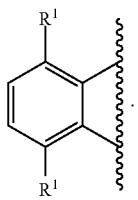

II

8. A compound which is selected from the group consisting of:

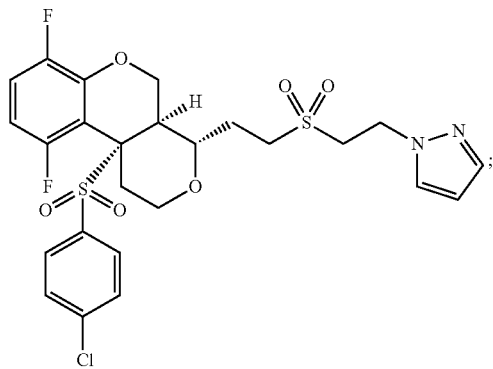

;

-continued

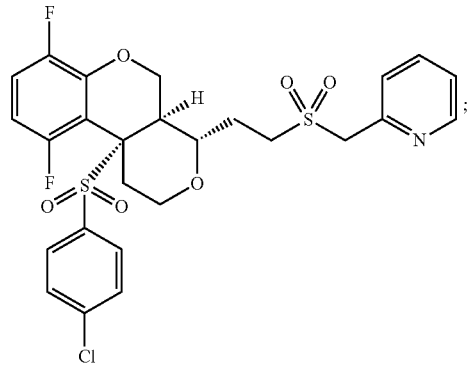

;

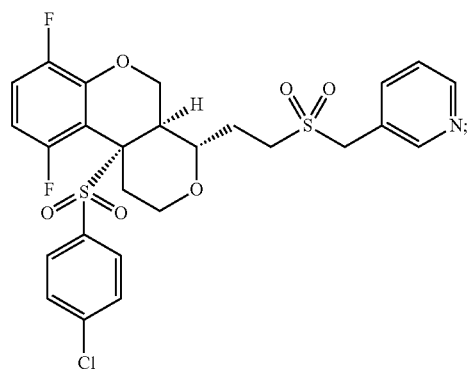

;

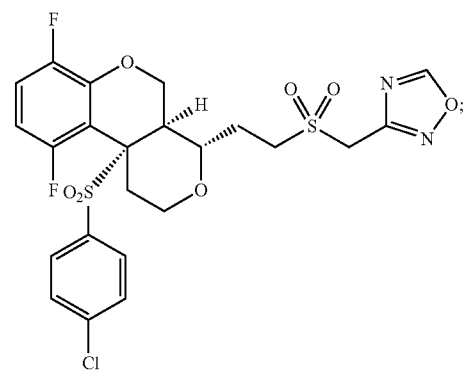

;

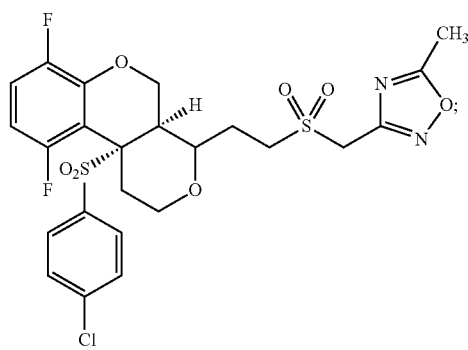

;

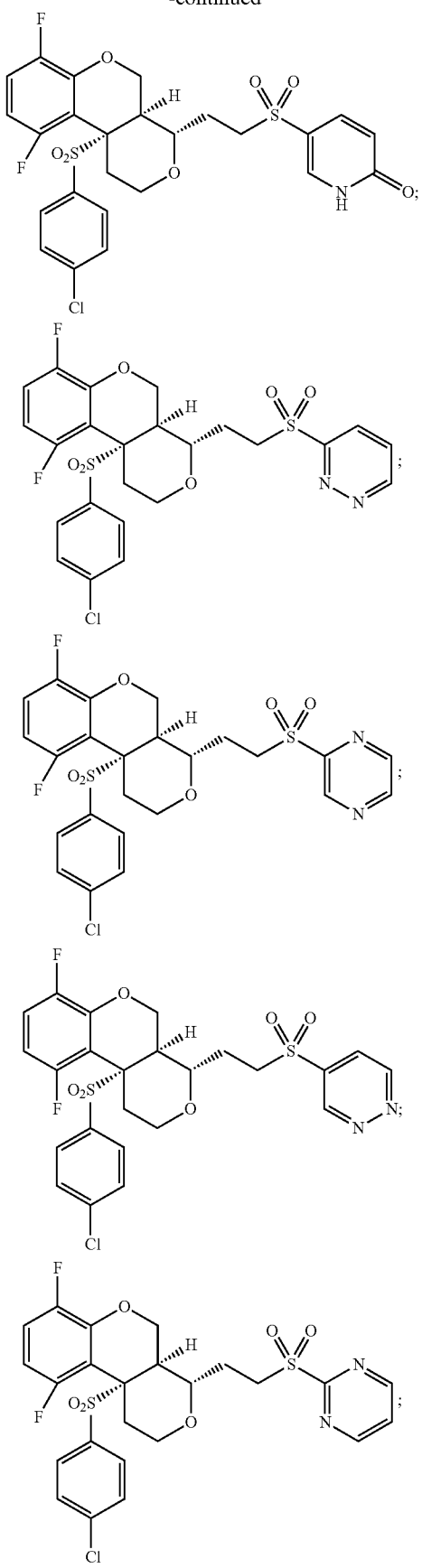
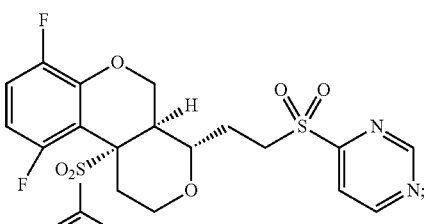
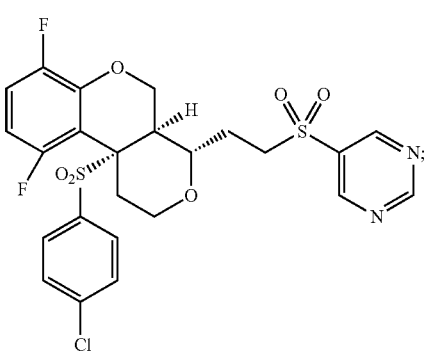
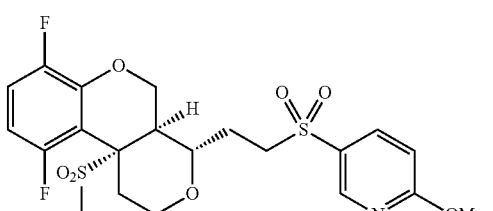
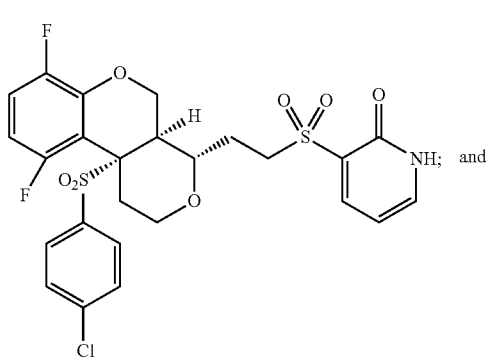

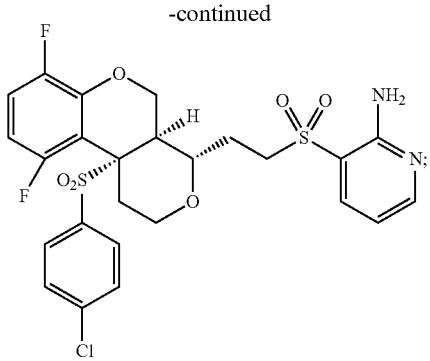

or a pharmaceutically acceptable salt thereof.

9. A compound which is selected from the group consisting of:

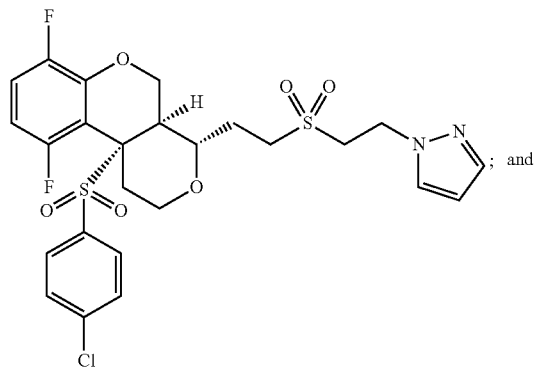

; and

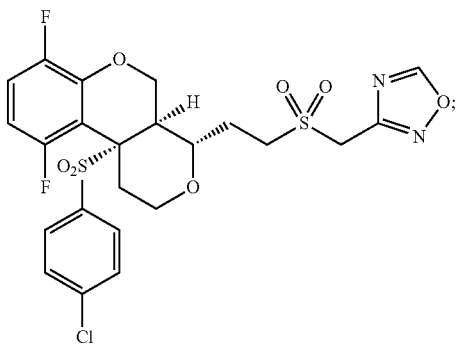

or a pharmaceutically acceptable salt thereof.

10. A pharmaceutical composition comprising the compound of claim 1, or a pharmaceutically acceptable salt thereof, and at least one pharmaceutically acceptable carrier.

11. A pharmaceutical composition comprising the compound of claim 8 or a pharmaceutically acceptable salt thereof, and at least one pharmaceutical acceptable carrier.

12. A pharmaceutical composition comprising the compound of claim 9 or a pharmaceutically acceptable salt thereof, and at least one pharmaceutical acceptable carrier.

* * * * *